(12) United States Patent
Wales et al.

(10) Patent No.: US 9,737,294 B2
(45) Date of Patent: Aug. 22, 2017

(54) METHOD AND SYSTEM FOR ORTHOPEDIC REPAIR

(71) Applicant: CARTIVA, INC., Alpharetta, GA (US)

(72) Inventors: Lawrence W. Wales, Maplewood, MN (US); Jeff Peters, Excelsior, MN (US)

(73) Assignee: Cartiva, Inc., Alpharetta, GA (US)

( * ) Notice: Subject to any disclaimer, the term of this patent is extended or adjusted under 35 U.S.C. 154(b) by 108 days.

(21) Appl. No.: 14/165,421

(22) Filed: Jan. 27, 2014

(65) Prior Publication Data

US 2014/0214080 A1 Jul. 31, 2014

Related U.S. Application Data

(60) Provisional application No. 61/757,553, filed on Jan. 28, 2013.

(51) Int. Cl.
*A61B 17/04* (2006.01)
*A61B 17/72* (2006.01)
*A61B 17/88* (2006.01)

(52) U.S. Cl.
CPC ...... *A61B 17/0401* (2013.01); *A61B 17/7291* (2013.01); *A61B 17/8869* (2013.01);
(Continued)

(58) Field of Classification Search
CPC ............ A61B 17/0401; A61B 17/7291; A61B 17/8866; A61B 17/8869; A61B 17/0466;
(Continued)

(56) References Cited

U.S. PATENT DOCUMENTS 3,131,957 A * 5/1964 Musto ............... A01K 91/04
289/17
3,648,705 A * 3/1972 Lary ................ A61B 17/0466
606/233

(Continued)

FOREIGN PATENT DOCUMENTS

DE 4323959501 7/1994
EP 0020021 12/1980

(Continued)

OTHER PUBLICATIONS

International Search Report and Written Opinion for related PCT application, PCT Application No. PCT/US2014/13242, mailed on Jun. 23, 2014 in 18 pages.

(Continued)

*Primary Examiner* — David C Eastwood
(74) *Attorney, Agent, or Firm* — Knobbe, Martens, Olson & Bear, LLP

(57) ABSTRACT

An implantable orthopedic repair device includes an implant body having a rigid tubular shape which defines an inner lumen and an orthogonal suture side hole in communication with the inner lumen. The implantable orthopedic repair device includes a tension assembly that is supported by the inner lumen and suture side hole of the implant body. The tension assembly includes a suture loop which defines a suture tail and a sliding knot that when tensioned contracts at least one bone anchor, independent of the implant body, unidirectionally towards the implant body.

18 Claims, 9 Drawing Sheets

(52) U.S. Cl.
CPC ............... *A61B 2017/0414* (2013.01); *A61B 2017/0427* (2013.01); *A61B 2017/0437* (2013.01); *A61B 2017/0445* (2013.01); *A61B 2017/0496* (2013.01)

(58) Field of Classification Search
CPC .... A61B 2017/0409; A61B 2017/0411; A61B 2017/0412; A61B 2017/0414; A61B 2017/0427; A61B 2017/0437; A61B 2017/0445; A61B 2017/0496; A61F 2/0811; A61F 2002/0817; A61F 2002/0823; A61F 2002/0829; A61F 2002/0841; A61F 2002/0847; A61F 2002/0852; A61F 2002/0876; A61F 2002/0882; A61F 2002/0888
See application file for complete search history.

(56) References Cited

U.S. PATENT DOCUMENTS

| | | |
|---|---|---|
| 3,752,516 A * | 8/1973 | Mumma ............... A01K 91/04 289/17 |
| 3,875,595 A | 4/1975 | Froning |
| 3,895,753 A | 7/1975 | Bone |
| 3,990,619 A | 11/1976 | Russell |
| 4,006,747 A | 2/1977 | Kronenthal et al. |
| 4,007,743 A | 2/1977 | Blake |
| 4,013,078 A | 3/1977 | Feild |
| 4,059,115 A | 11/1977 | Jumashev et al. |
| 4,224,413 A | 9/1980 | Burbidge |
| 4,235,238 A * | 11/1980 | Ogiu ............... A61B 17/04 606/145 |
| 4,502,161 A | 3/1985 | Wall |
| 4,512,338 A | 4/1985 | Balko et al. |
| 4,532,926 A | 8/1985 | O'Holla |
| 4,545,374 A | 10/1985 | Jacobson |
| 4,602,635 A | 7/1986 | Mulhollan et al. |
| 4,626,665 A | 12/1986 | Fort, III |
| 4,632,100 A | 12/1986 | Somers et al. |
| 4,662,886 A | 5/1987 | Moorse et al. |
| 4,663,358 A | 5/1987 | Hyon et al. |
| 4,669,473 A | 6/1987 | Richards et al. |
| 4,678,459 A | 7/1987 | Onik et al. |
| 4,731,084 A | 3/1988 | Dunn et al. |
| 4,736,746 A | 4/1988 | Anderson |
| 4,741,330 A | 5/1988 | Hayhurst |
| 4,743,260 A | 5/1988 | Burton |
| 4,744,364 A | 5/1988 | Kensey |
| 4,772,287 A | 9/1988 | Ray et al. |
| 4,781,190 A | 11/1988 | Lee |
| 4,790,850 A | 12/1988 | Dunn et al. |
| 4,798,205 A | 1/1989 | Bonomo et al. |
| 4,834,757 A | 5/1989 | Brantigan |
| 4,837,285 A | 6/1989 | Berg et al. |
| 4,844,088 A | 7/1989 | Kambin |
| 4,852,568 A | 8/1989 | Kensey |
| 4,863,477 A | 9/1989 | Monson |
| 4,873,976 A | 10/1989 | Schreiber |
| 4,884,572 A | 12/1989 | Bays et al. |
| 4,890,612 A | 1/1990 | Kensey |
| 4,895,148 A | 1/1990 | Bays et al. |
| 4,898,156 A | 2/1990 | Gatturna et al. |
| 4,904,260 A | 2/1990 | Ray et al. |
| 4,904,261 A | 2/1990 | Dove et al. |
| 4,911,718 A | 3/1990 | Lee et al. |
| 4,917,704 A | 4/1990 | Frey et al. |
| 4,919,667 A | 4/1990 | Richmond |
| 4,932,969 A | 6/1990 | Frey et al. |
| 4,946,377 A | 8/1990 | Kovach |
| 4,946,378 A | 8/1990 | Hirayama et al. |
| 4,955,908 A | 9/1990 | Frey et al. |
| 4,959,069 A | 9/1990 | Brennan et al. |
| 4,976,715 A | 12/1990 | Bays et al. |
| 5,002,576 A | 3/1991 | Fuhrmann et al. |
| 5,015,255 A | 5/1991 | Kuslich |
| 5,021,059 A | 6/1991 | Kensey et al. |
| 5,035,716 A | 7/1991 | Downey |
| 5,041,129 A | 8/1991 | Hayhurst et al. |
| 5,047,055 A | 9/1991 | Bao et al. |
| 5,053,046 A | 10/1991 | Janese |
| 5,059,193 A | 10/1991 | Kuslich |
| 5,059,206 A | 10/1991 | Winters |
| 5,061,274 A | 10/1991 | Kensey |
| 5,062,344 A | 11/1991 | Gerker |
| 5,071,437 A | 12/1991 | Steffee |
| 5,085,661 A | 2/1992 | Moss |
| 5,100,422 A | 3/1992 | Berguer et al. |
| 5,108,420 A | 4/1992 | Marks |
| 5,108,438 A | 4/1992 | Stone |
| 5,116,357 A | 5/1992 | Eberbach |
| 5,122,154 A | 6/1992 | Rhodes |
| 5,122,155 A | 6/1992 | Eberbach |
| 5,123,913 A | 6/1992 | Wilk et al. |
| 5,123,926 A | 6/1992 | Pisharodi |
| 5,129,912 A | 7/1992 | Noda et al. |
| 5,141,515 A | 8/1992 | Eberbach |
| 5,147,374 A | 9/1992 | Fernandez |
| 5,171,259 A | 12/1992 | Inoue |
| 5,171,278 A | 12/1992 | Pisharodi |
| 5,171,280 A | 12/1992 | Baumgartner |
| 5,171,281 A | 12/1992 | Parsons et al. |
| 5,176,682 A | 1/1993 | Chow |
| 5,176,691 A | 1/1993 | Pierce |
| 5,176,692 A | 1/1993 | Wilk et al. |
| 5,192,326 A | 3/1993 | Bao et al. |
| 5,195,541 A | 3/1993 | Obenchain |
| 5,203,787 A | 4/1993 | Noblitt et al. |
| 5,204,106 A | 4/1993 | Schepers et al. |
| 5,207,695 A | 5/1993 | Trout, III |
| 5,211,650 A | 5/1993 | Noda |
| 5,222,962 A | 6/1993 | Burkhart |
| 5,222,974 A | 6/1993 | Kensey et al. |
| 5,224,946 A | 7/1993 | Hayhurst et al. |
| 5,242,439 A | 9/1993 | Larsen et al. |
| 5,254,133 A | 10/1993 | Seid |
| 5,258,000 A | 11/1993 | Gianturco |
| 5,258,043 A | 11/1993 | Stone |
| 5,269,783 A | 12/1993 | Sander |
| 5,269,791 A | 12/1993 | Mayzels et al. |
| 5,269,809 A | 12/1993 | Hayhurst et al. |
| 5,282,827 A | 2/1994 | Kensey et al. |
| 5,282,863 A | 2/1994 | Burton |
| 5,304,194 A | 4/1994 | Chee et al. |
| 5,306,311 A | 4/1994 | Stone et al. |
| 5,312,435 A | 5/1994 | Nash et al. |
| 5,313,962 A | 5/1994 | Obenchain |
| 5,318,575 A | 6/1994 | Chesterfield et al. |
| 5,320,629 A | 6/1994 | Noda et al. |
| 5,320,633 A | 6/1994 | Allen et al. |
| 5,320,644 A | 6/1994 | Baumgartner |
| 5,342,393 A | 8/1994 | Stack |
| 5,342,394 A | 8/1994 | Matsuno et al. |
| 5,344,442 A | 9/1994 | Deac |
| 5,354,736 A | 10/1994 | Bhatnagar |
| 5,356,432 A | 10/1994 | Rutkow et al. |
| 5,366,460 A | 11/1994 | Eberbach |
| 5,368,602 A | 11/1994 | de la Torre |
| 5,370,660 A | 12/1994 | Weinstein et al. |
| 5,370,662 A | 12/1994 | Stone et al. |
| 5,370,697 A | 12/1994 | Baumgartner |
| 5,374,268 A | 12/1994 | Sander |
| 5,376,120 A | 12/1994 | Sarver et al. |
| 5,383,477 A | 1/1995 | DeMatteis |
| 5,383,905 A | 1/1995 | Golds et al. |
| 5,390,683 A | 2/1995 | Pisharodi |
| 5,391,182 A | 2/1995 | Chin |
| 5,397,326 A | 3/1995 | Mangum |
| 5,397,331 A | 3/1995 | Himpens et al. |
| 5,397,332 A | 3/1995 | Kammerer et al. |
| 5,397,991 A | 3/1995 | Rogers |
| 5,398,861 A | 3/1995 | Green |
| 5,405,352 A | 4/1995 | Weston |
| 5,405,359 A | 4/1995 | Pierce |

(56) References Cited

U.S. PATENT DOCUMENTS

| | | | |
|---|---|---|---|
| 5,405,360 A | 4/1995 | Tovey | |
| 5,411,523 A | 5/1995 | Goble | |
| 5,417,691 A | 5/1995 | Hayhurst | |
| 5,417,699 A | 5/1995 | Klein et al. | |
| 5,417,712 A | 5/1995 | Whittaker et al. | |
| 5,425,772 A | 6/1995 | Brantigan | |
| 5,425,773 A | 6/1995 | Boyd et al. | |
| 5,429,598 A | 7/1995 | Waxman et al. | |
| 5,437,631 A | 8/1995 | Janzen | |
| 5,437,680 A | 8/1995 | Yoon | |
| 5,439,464 A | 8/1995 | Shapiro | |
| 5,441,502 A | 8/1995 | Bartlett | |
| 5,456,720 A | 10/1995 | Schultz et al. | |
| 5,464,407 A | 11/1995 | McGuire | |
| 5,464,425 A | 11/1995 | Skiba | |
| 5,464,426 A | 11/1995 | Bonutti | |
| 5,464,427 A * | 11/1995 | Curtis | A61B 17/0401 411/60.1 |
| 5,470,337 A | 11/1995 | Moss | |
| 5,489,307 A | 2/1996 | Kuslich et al. | |
| 5,492,697 A | 2/1996 | Boyan et al. | |
| 5,496,348 A | 3/1996 | Bonutti | |
| 5,500,000 A | 3/1996 | Feagin et al. | |
| 5,507,754 A | 4/1996 | Green et al. | |
| 5,507,755 A | 4/1996 | Gresl et al. | |
| 5,514,180 A | 5/1996 | Heggeness et al. | |
| 5,520,696 A | 5/1996 | Wenstrom, Jr. | |
| 5,520,700 A | 5/1996 | Beyar et al. | |
| 5,527,342 A | 6/1996 | Pietrzak et al. | |
| 5,527,343 A | 6/1996 | Bonutti | |
| 5,529,075 A | 6/1996 | Clark | |
| 5,531,678 A | 7/1996 | Tomba et al. | |
| 5,531,759 A | 7/1996 | Kensey et al. | |
| 5,534,012 A | 7/1996 | Bonutti | |
| 5,534,028 A | 7/1996 | Bao et al. | |
| 5,534,030 A | 7/1996 | Navarro et al. | |
| 5,540,703 A | 7/1996 | Barker, Jr. et al. | |
| 5,540,704 A | 7/1996 | Gordon et al. | |
| 5,540,715 A | 7/1996 | Katsaros et al. | |
| 5,545,178 A | 8/1996 | Kensey et al. | |
| 5,545,229 A | 8/1996 | Parsons et al. | |
| 5,549,617 A | 8/1996 | Green et al. | |
| 5,549,679 A | 8/1996 | Kuslich | |
| 5,556,428 A | 9/1996 | Shah | |
| 5,556,429 A | 9/1996 | Felt | |
| 5,562,684 A | 10/1996 | Kammerer | |
| 5,562,689 A | 10/1996 | Green et al. | |
| 5,562,736 A | 10/1996 | Ray et al. | |
| 5,562,738 A | 10/1996 | Boyd et al. | |
| 5,569,242 A | 10/1996 | Lax et al. | |
| 5,569,252 A | 10/1996 | Justin et al. | |
| 5,569,303 A | 10/1996 | Johnson | |
| 5,569,306 A | 10/1996 | Thal | |
| 5,571,189 A | 11/1996 | Kuslich | |
| 5,573,286 A | 11/1996 | Rogozinski | |
| 5,573,548 A | 11/1996 | Nazre et al. | |
| 5,578,057 A | 11/1996 | Wenstrom, Jr. | |
| 5,582,616 A | 12/1996 | Bolduc et al. | |
| 5,584,862 A | 12/1996 | Bonutti | |
| 5,591,177 A | 1/1997 | Lehrer | |
| 5,591,223 A | 1/1997 | Lock et al. | |
| 5,593,425 A | 1/1997 | Bonutti et al. | |
| 5,599,279 A | 2/1997 | Slotman et al. | |
| 5,601,557 A | 2/1997 | Hayhurst | |
| 5,601,571 A | 2/1997 | Moss | |
| 5,613,974 A | 3/1997 | Andreas et al. | |
| 5,618,314 A | 4/1997 | Harwin et al. | |
| 5,620,012 A | 4/1997 | Benderev et al. | |
| 5,624,463 A | 4/1997 | Stone et al. | |
| 5,626,612 A | 5/1997 | Bartlett | |
| 5,626,613 A | 5/1997 | Schmieding | |
| 5,626,614 A | 5/1997 | Hart | |
| 5,628,756 A | 5/1997 | Barker, Jr. et al. | |
| 5,634,931 A | 6/1997 | Kugel | |
| 5,634,944 A | 6/1997 | Magram | |
| 5,643,319 A | 7/1997 | Green et al. | |
| 5,643,320 A | 7/1997 | Lower et al. | |
| 5,645,084 A | 7/1997 | McKay | |
| 5,645,597 A | 7/1997 | Krapiva | |
| 5,647,874 A | 7/1997 | Hayhurst | |
| 5,649,945 A | 7/1997 | Ray et al. | |
| 5,658,343 A | 8/1997 | Hauselmann et al. | |
| 5,662,658 A | 9/1997 | Wenstrom, Jr. | |
| 5,662,681 A | 9/1997 | Nash et al. | |
| 5,662,683 A | 9/1997 | Kay | |
| 5,669,935 A | 9/1997 | Rosenman et al. | |
| 5,674,294 A | 10/1997 | Bainville et al. | |
| 5,674,296 A | 10/1997 | Bryan et al. | |
| 5,676,698 A | 10/1997 | Janzen et al. | |
| 5,676,701 A | 10/1997 | Yuan et al. | |
| 5,681,310 A | 10/1997 | Yuan et al. | |
| 5,681,351 A | 10/1997 | Jamiolkowski et al. | |
| 5,683,417 A | 11/1997 | Cooper | |
| 5,683,418 A | 11/1997 | Luscombe et al. | |
| 5,683,419 A | 11/1997 | Thal | |
| 5,683,465 A | 11/1997 | Shinn et al. | |
| 5,690,677 A | 11/1997 | Schmieding et al. | |
| 5,695,525 A | 12/1997 | Mulhauser et al. | |
| 5,697,950 A | 12/1997 | Fucci et al. | |
| 5,699,657 A | 12/1997 | Paulson | |
| 5,702,449 A | 12/1997 | McKay | |
| 5,702,450 A | 12/1997 | Bisserie | |
| 5,702,451 A | 12/1997 | Biedermann et al. | |
| 5,702,454 A | 12/1997 | Baumgartner | |
| 5,702,462 A | 12/1997 | Oberlander | |
| 5,704,943 A | 1/1998 | Yoon et al. | |
| 5,709,708 A | 1/1998 | Thal | |
| 5,716,404 A | 2/1998 | Vacanti et al. | |
| 5,716,408 A | 2/1998 | Eldridge et al. | |
| 5,716,409 A | 2/1998 | Debbas | |
| 5,716,413 A | 2/1998 | Walter et al. | |
| 5,716,416 A | 2/1998 | Lin | |
| 5,718,717 A | 2/1998 | Bonutti | |
| 5,725,552 A | 3/1998 | Kotula et al. | |
| 5,725,577 A | 3/1998 | Saxon | |
| 5,728,109 A | 3/1998 | Schulze et al. | |
| 5,728,150 A | 3/1998 | McDonald et al. | |
| 5,730,744 A | 3/1998 | Justin et al. | |
| 5,733,307 A | 3/1998 | Dinsdale | |
| 5,733,337 A | 3/1998 | Carr, Jr. et al. | |
| 5,735,875 A | 4/1998 | Bonutti et al. | |
| 5,736,746 A | 4/1998 | Furutoh | |
| 5,743,917 A | 4/1998 | Saxon | |
| 5,746,755 A | 5/1998 | Wood et al. | |
| 5,752,964 A | 5/1998 | Mericle | |
| 5,755,797 A | 5/1998 | Baumgartner | |
| 5,759,189 A | 6/1998 | Ferragamo et al. | |
| 5,766,246 A | 6/1998 | Mulhauser et al. | |
| 5,769,864 A | 6/1998 | Kugel | |
| 5,769,893 A | 6/1998 | Shah | |
| 5,772,661 A | 6/1998 | Michelson | |
| 5,776,183 A | 7/1998 | Kanesaka et al. | |
| 5,782,844 A | 7/1998 | Yoon et al. | |
| 5,782,860 A | 7/1998 | Epstein et al. | |
| 5,782,864 A | 7/1998 | Lizardi | |
| 5,785,705 A | 7/1998 | Baker | |
| 5,786,217 A | 7/1998 | Tubo et al. | |
| 5,788,625 A | 8/1998 | Plouhar et al. | |
| 5,792,152 A | 8/1998 | Klein et al. | |
| 5,797,929 A | 8/1998 | Andreas et al. | |
| 5,800,549 A | 9/1998 | Bao et al. | |
| 5,800,550 A | 9/1998 | Sertich | |
| 5,810,848 A | 9/1998 | Hayhurst | |
| 5,810,851 A | 9/1998 | Yoon | |
| 5,814,051 A | 9/1998 | Wenstrom, Jr. | |
| 5,823,994 A | 10/1998 | Sharkey et al. | |
| 5,824,008 A | 10/1998 | Bolduc et al. | |
| 5,824,011 A | 10/1998 | Stone et al. | |
| 5,824,082 A | 10/1998 | Brown | |
| 5,824,093 A | 10/1998 | Ray et al. | |
| 5,824,094 A | 10/1998 | Serhan et al. | |
| 5,827,298 A | 10/1998 | Hart et al. | |
| 5,827,325 A | 10/1998 | Landgrebe et al. | |
| 5,827,328 A | 10/1998 | Buttermann | |

(56) References Cited

U.S. PATENT DOCUMENTS

| | | |
|---|---|---|
| 5,836,315 A | 11/1998 | Benderev et al. |
| 5,842,477 A | 12/1998 | Naughton et al. |
| 5,843,084 A | 12/1998 | Hart et al. |
| 5,846,261 A | 12/1998 | Kotula et al. |
| 5,849,331 A | 12/1998 | Ducheyne et al. |
| 5,851,219 A | 12/1998 | Goble et al. |
| 5,853,422 A | 12/1998 | Huebsch et al. |
| 5,855,614 A | 1/1999 | Stevens et al. |
| 5,860,425 A | 1/1999 | Benderev et al. |
| 5,860,977 A | 1/1999 | Zucherman et al. |
| 5,865,845 A | 2/1999 | Thalgott |
| 5,865,846 A | 2/1999 | Bryan et al. |
| 5,868,762 A | 2/1999 | Cragg et al. |
| 5,879,366 A | 3/1999 | Shaw et al. |
| 5,888,220 A | 3/1999 | Felt et al. |
| 5,888,222 A | 3/1999 | Coates et al. |
| 5,888,226 A | 3/1999 | Rogozinski |
| 5,891,146 A | 4/1999 | Simon et al. |
| 5,893,592 A | 4/1999 | Schulze et al. |
| 5,893,889 A | 4/1999 | Harrington |
| 5,895,426 A | 4/1999 | Scarborough et al. |
| 5,899,920 A | 5/1999 | DeSatnick et al. |
| 5,904,703 A | 5/1999 | Gilson |
| 5,916,225 A | 6/1999 | Kugel |
| 5,919,235 A | 7/1999 | Husson et al. |
| 5,922,026 A | 7/1999 | Chin |
| 5,922,028 A | 7/1999 | Plouhar et al. |
| 5,928,284 A | 7/1999 | Mehdizadeh |
| 5,935,147 A | 8/1999 | Kensey et al. |
| 5,941,439 A | 8/1999 | Kammerer et al. |
| 5,944,738 A | 8/1999 | Amplatz et al. |
| 5,948,001 A | 9/1999 | Larsen |
| 5,948,002 A | 9/1999 | Bonutti |
| 5,954,716 A | 9/1999 | Sharkey et al. |
| 5,954,767 A | 9/1999 | Pajotin et al. |
| 5,957,939 A | 9/1999 | Heaven et al. |
| 5,957,953 A | 9/1999 | DiPoto et al. |
| 5,961,538 A | 10/1999 | Pedlick et al. |
| 5,964,783 A | 10/1999 | Grafton et al. |
| 5,964,807 A | 10/1999 | Gan et al. |
| 5,970,697 A | 10/1999 | Jacobs et al. |
| 5,972,000 A | 10/1999 | Beyar et al. |
| 5,972,007 A | 10/1999 | Sheffield et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 5,980,558 A | 11/1999 | Wiley |
| 5,981,826 A | 11/1999 | Ku et al. |
| 5,984,948 A | 11/1999 | Hasson |
| 6,001,130 A | 12/1999 | Bryan et al. |
| 6,007,567 A | 12/1999 | Bonutti |
| 6,007,570 A | 12/1999 | Sharkey et al. |
| 6,007,575 A | 12/1999 | Samuels |
| 6,010,525 A | 1/2000 | Bonutti et al. |
| 6,019,792 A | 2/2000 | Cauthen |
| 6,019,793 A | 2/2000 | Perren et al. |
| 6,024,096 A | 2/2000 | Buckberg |
| 6,024,754 A | 2/2000 | Engelson |
| 6,024,758 A | 2/2000 | Thal |
| 6,027,523 A | 2/2000 | Schmieding |
| 6,027,527 A | 2/2000 | Asano et al. |
| 6,036,699 A | 3/2000 | Andreas et al. |
| 6,039,761 A | 3/2000 | Li et al. |
| 6,039,762 A | 3/2000 | McKay |
| 6,045,561 A | 4/2000 | Marshall et al. |
| 6,045,573 A | 4/2000 | Wenstrom, Jr. et al. |
| 6,053,909 A | 4/2000 | Shadduck |
| 6,063,378 A | 5/2000 | Nohara et al. |
| 6,066,146 A | 5/2000 | Carroll et al. |
| 6,066,776 A | 5/2000 | Goodwin et al. |
| 6,068,648 A | 5/2000 | Cole et al. |
| 6,073,051 A | 6/2000 | Sharkey et al. |
| 6,080,182 A | 6/2000 | Shaw et al. |
| 6,093,205 A | 7/2000 | McLeod et al. |
| 6,095,149 A | 8/2000 | Sharkey et al. |
| 6,099,514 A | 8/2000 | Sharkey et al. |
| 6,102,934 A | 8/2000 | Li |
| 6,106,545 A | 8/2000 | Egan |
| 6,113,609 A | 9/2000 | Adams |
| 6,113,623 A | 9/2000 | Sgro |
| 6,113,639 A | 9/2000 | Ray et al. |
| 6,117,162 A | 9/2000 | Schmieding et al. |
| 6,123,715 A | 9/2000 | Amplatz |
| 6,126,682 A | 10/2000 | Sharkey et al. |
| 6,139,565 A | 10/2000 | Stone et al. |
| 6,140,452 A | 10/2000 | Felt et al. |
| 6,143,006 A | 11/2000 | Chan |
| 6,143,017 A | 11/2000 | Thal |
| 6,146,380 A | 11/2000 | Racz et al. |
| 6,146,406 A | 11/2000 | Shluzas et al. |
| 6,146,422 A | 11/2000 | Lawson |
| 6,162,203 A | 12/2000 | Haaga |
| 6,168,598 B1 | 1/2001 | Martello |
| 6,171,317 B1 | 1/2001 | Jackson et al. |
| 6,171,318 B1 | 1/2001 | Kugel et al. |
| 6,171,329 B1 | 1/2001 | Shaw et al. |
| 6,174,322 B1 | 1/2001 | Schneidt |
| 6,176,863 B1 | 1/2001 | Kugel et al. |
| 6,179,874 B1 | 1/2001 | Cauthen |
| 6,179,879 B1 | 1/2001 | Robinson et al. |
| 6,183,518 B1 | 2/2001 | Ross et al. |
| 6,187,048 B1 | 2/2001 | Milner et al. |
| 6,190,401 B1 | 2/2001 | Green et al. |
| 6,200,329 B1 | 3/2001 | Fung et al. |
| 6,203,554 B1 | 3/2001 | Roberts |
| 6,203,565 B1 | 3/2001 | Bonutti et al. |
| 6,206,895 B1 | 3/2001 | Levinson |
| 6,206,921 B1 | 3/2001 | Guagliano et al. |
| 6,221,092 B1 | 4/2001 | Koike et al. |
| 6,221,109 B1 | 4/2001 | Geistlich et al. |
| 6,224,630 B1 | 5/2001 | Bao et al. |
| 6,228,096 B1 | 5/2001 | Marchand |
| 6,231,605 B1 | 5/2001 | Ku |
| 6,231,615 B1 | 5/2001 | Preissman |
| 6,241,768 B1 | 6/2001 | Agarwal et al. |
| 6,245,080 B1 | 6/2001 | Levinson |
| 6,245,107 B1 | 6/2001 | Ferree |
| 6,248,106 B1 | 6/2001 | Ferree |
| 6,248,131 B1 | 6/2001 | Felt et al. |
| 6,258,094 B1 | 7/2001 | Nicholson et al. |
| 6,264,677 B1 | 7/2001 | Simon et al. |
| 6,267,772 B1 | 7/2001 | Mulhauser et al. |
| 6,280,453 B1 | 8/2001 | Kugel et al. |
| 6,287,324 B1 | 9/2001 | Yarnitsky et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,306,177 B1 | 10/2001 | Felt et al. |
| 6,312,448 B1 | 11/2001 | Bonutti |
| 6,319,263 B1 | 11/2001 | Levinson |
| 6,332,894 B1 | 12/2001 | Stalcup et al. |
| 6,340,369 B1 | 1/2002 | Ferree |
| 6,342,064 B1 | 1/2002 | Koike et al. |
| 6,344,057 B1 | 2/2002 | Rabbe et al. |
| 6,344,058 B1 | 2/2002 | Ferree |
| 6,352,557 B1 | 3/2002 | Ferree |
| 6,355,052 B1 | 3/2002 | Neuss et al. |
| 6,364,897 B1 | 4/2002 | Bonutti |
| 6,371,984 B1 | 4/2002 | Van Dyke et al. |
| 6,371,990 B1 | 4/2002 | Ferree |
| 6,391,060 B1 | 5/2002 | Ory et al. |
| 6,402,750 B1 | 6/2002 | Atkinson et al. |
| 6,402,784 B1 | 6/2002 | Wardlaw |
| 6,402,785 B1 | 6/2002 | Zdeblick et al. |
| 6,409,739 B1 | 6/2002 | Nobles et al. |
| 6,419,676 B1 | 7/2002 | Zucherman et al. |
| 6,419,702 B1 | 7/2002 | Ferree |
| 6,419,703 B1 | 7/2002 | Fallin et al. |
| 6,419,704 B1 | 7/2002 | Ferree |
| 6,419,706 B1 | 7/2002 | Graf |
| 6,423,065 B2 | 7/2002 | Ferree |
| 6,423,080 B1 | 7/2002 | Gellman et al. |
| 6,425,919 B1 | 7/2002 | Lambrecht |

(56) References Cited

U.S. PATENT DOCUMENTS

| | | |
|---|---|---|
| 6,425,924 B1 | 7/2002 | Rousseau |
| 6,428,562 B2 | 8/2002 | Bonutti |
| 6,428,576 B1 | 8/2002 | Haldimann |
| 6,432,107 B1 | 8/2002 | Ferree |
| 6,432,123 B2 | 8/2002 | Schwartz et al. |
| 6,436,098 B1 | 8/2002 | Michelson |
| 6,436,099 B1 | 8/2002 | Drewry et al. |
| 6,436,143 B1 | 8/2002 | Ross et al. |
| 6,443,988 B2 | 9/2002 | Felt et al. |
| 6,447,531 B1 | 9/2002 | Amplatz |
| 6,452,924 B1 | 9/2002 | Golden et al. |
| 6,454,804 B1 | 9/2002 | Ferree |
| 6,464,712 B1 | 10/2002 | Epstein et al. |
| 6,482,235 B1 | 11/2002 | Lambrecht et al. |
| 6,488,691 B1 | 12/2002 | Carroll et al. |
| 6,491,724 B1 | 12/2002 | Ferree |
| 6,494,883 B1 | 12/2002 | Ferree |
| 6,500,132 B1 | 12/2002 | Li |
| 6,500,184 B1 | 12/2002 | Chan et al. |
| 6,508,828 B1 | 1/2003 | Akerfeldt et al. |
| 6,508,839 B1 | 1/2003 | Lambrecht et al. |
| 6,511,488 B1 | 1/2003 | Marshall et al. |
| 6,511,498 B1 | 1/2003 | Fumex |
| 6,511,958 B1 | 1/2003 | Atkinson et al. |
| 6,514,255 B1 | 2/2003 | Ferree |
| 6,514,514 B1 | 2/2003 | Atkinson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,530,933 B1 | 3/2003 | Yeung et al. |
| 6,533,799 B1 | 3/2003 | Bouchier |
| 6,533,817 B1 | 3/2003 | Norton et al. |
| 6,544,267 B1 | 4/2003 | Cole et al. |
| 6,547,800 B2 | 4/2003 | Foerster et al. |
| 6,547,806 B1 | 4/2003 | Ding |
| 6,558,386 B1 | 5/2003 | Cragg |
| 6,558,390 B2 | 5/2003 | Cragg |
| 6,562,052 B2 | 5/2003 | Nobles et al. |
| 6,569,187 B1 | 5/2003 | Bonutti et al. |
| 6,569,442 B2 | 5/2003 | Gan et al. |
| 6,572,635 B1 | 6/2003 | Bonutti |
| 6,572,653 B1 | 6/2003 | Simonson |
| 6,575,979 B1 | 6/2003 | Cragg |
| 6,576,017 B2 | 6/2003 | Foley et al. |
| 6,579,291 B1 | 6/2003 | Keith et al. |
| 6,582,453 B1 | 6/2003 | Tran et al. |
| 6,592,608 B2 | 7/2003 | Fisher et al. |
| 6,592,609 B1 | 7/2003 | Bonutti |
| 6,592,625 B2 | 7/2003 | Cauthen |
| 6,596,012 B2 | 7/2003 | Akerfeldt et al. |
| 6,602,291 B1 | 8/2003 | Ray et al. |
| 6,605,096 B1 | 8/2003 | Ritchart |
| 6,607,541 B1 | 8/2003 | Gardiner et al. |
| 6,610,006 B1 | 8/2003 | Amid et al. |
| 6,610,071 B1 | 8/2003 | Cohn et al. |
| 6,610,079 B1 | 8/2003 | Li et al. |
| 6,610,091 B1 | 8/2003 | Reiley |
| 6,610,666 B1 | 8/2003 | Åkerblom |
| 6,613,044 B2 | 9/2003 | Carl |
| 6,620,185 B1 | 9/2003 | Harvie et al. |
| 6,620,196 B1 | 9/2003 | Trieu |
| 6,623,492 B1 | 9/2003 | Berube et al. |
| 6,623,508 B2 | 9/2003 | Shaw et al. |
| 6,625,073 B1 | 9/2003 | Beffa |
| 6,626,899 B2 | 9/2003 | Houser et al. |
| 6,626,916 B1 | 9/2003 | Yeung et al. |
| 6,645,227 B2 | 11/2003 | Fallin et al. |
| 6,645,247 B2 | 11/2003 | Ferree |
| 6,648,890 B2 | 11/2003 | Culbert et al. |
| 6,648,892 B2 | 11/2003 | Martello |
| 6,648,918 B2 | 11/2003 | Ferree |
| 6,648,919 B2 | 11/2003 | Ferree |
| 6,648,920 B2 | 11/2003 | Ferree |
| 6,652,561 B1 | 11/2003 | Tran |
| 6,652,585 B2 | 11/2003 | Lange |
| 6,656,182 B1 | 12/2003 | Hayhurst |
| 6,656,183 B2 | 12/2003 | Colleran et al. |
| 6,669,687 B1 | 12/2003 | Saadat |
| 6,669,707 B1 | 12/2003 | Swanstrom et al. |
| 6,669,729 B2 | 12/2003 | Chin |
| 6,673,088 B1 | 1/2004 | Vargas et al. |
| 6,676,665 B2 | 1/2004 | Foley et al. |
| 6,679,887 B2 | 1/2004 | Nicholson et al. |
| 6,679,914 B1 | 1/2004 | Gabbay |
| 6,684,886 B1 | 2/2004 | Alleyne |
| 6,685,695 B2 | 2/2004 | Ferree |
| 6,685,728 B2 | 2/2004 | Sinnott et al. |
| 6,689,125 B1 | 2/2004 | Keith et al. |
| 6,692,506 B1 | 2/2004 | Ory et al. |
| 6,695,858 B1 | 2/2004 | Dubrul et al. |
| 6,696,073 B2 | 2/2004 | Boyce et al. |
| 6,699,263 B2 | 3/2004 | Cope |
| 6,706,068 B2 | 3/2004 | Ferree |
| 6,712,836 B1 | 3/2004 | Berg et al. |
| 6,712,837 B2 | 3/2004 | Akerfeldt et al. |
| 6,712,853 B2 | 3/2004 | Kuslich |
| 6,716,216 B1 | 4/2004 | Boucher et al. |
| 6,716,234 B2 | 4/2004 | Grafton et al. |
| 6,719,761 B1 | 4/2004 | Reiley et al. |
| 6,719,773 B1 | 4/2004 | Boucher et al. |
| 6,719,797 B1 | 4/2004 | Ferree |
| 6,723,058 B2 | 4/2004 | Li |
| 6,723,095 B2 | 4/2004 | Hammerslag |
| 6,723,097 B2 | 4/2004 | Fraser et al. |
| 6,723,107 B1 | 4/2004 | Skiba et al. |
| 6,723,133 B1 | 4/2004 | Pajotin |
| 6,723,335 B1 | 4/2004 | Moehlenbruck et al. |
| 6,726,721 B2 | 4/2004 | Stoy et al. |
| 6,730,092 B2 | 5/2004 | Songer |
| 6,730,112 B2 | 5/2004 | Levinson |
| 6,733,531 B1 | 5/2004 | Trieu |
| 6,733,534 B2 | 5/2004 | Sherman |
| 6,736,815 B2 | 5/2004 | Ginn |
| 6,740,093 B2 | 5/2004 | Hochschuler et al. |
| 6,743,255 B2 | 6/2004 | Ferree |
| 6,752,831 B2 | 6/2004 | Sybert et al. |
| 6,758,863 B2 | 7/2004 | Estes et al. |
| 6,761,720 B1 | 7/2004 | Senegas |
| 6,761,722 B2 | 7/2004 | Cole et al. |
| 6,764,514 B1 | 7/2004 | Li et al. |
| 6,767,037 B2 | 7/2004 | Wenstrom, Jr. |
| 6,770,076 B2 | 8/2004 | Foerster |
| 6,773,436 B2 | 8/2004 | Donnelly et al. |
| 6,773,699 B1 | 8/2004 | Soltz et al. |
| 6,780,198 B1 | 8/2004 | Gregoire et al. |
| 6,783,546 B2 | 8/2004 | Zucherman et al. |
| 6,805,695 B2 | 10/2004 | Keith et al. |
| 6,805,697 B1 | 10/2004 | Helm et al. |
| 6,805,715 B2 | 10/2004 | Reuter et al. |
| 6,812,211 B2 | 11/2004 | Slivka et al. |
| 6,821,276 B2 | 11/2004 | Lambrecht et al. |
| 6,824,562 B2 | 11/2004 | Mathis et al. |
| 6,827,716 B2 | 12/2004 | Ryan et al. |
| 6,827,743 B2 | 12/2004 | Eisermann et al. |
| 6,830,570 B1 | 12/2004 | Frey et al. |
| 6,833,006 B2 | 12/2004 | Foley et al. |
| 6,835,205 B2 | 12/2004 | Atkinson et al. |
| 6,835,207 B2 | 12/2004 | Zacouto et al. |
| 6,835,208 B2 | 12/2004 | Marchosky |
| 6,841,150 B2 | 1/2005 | Halvorsen et al. |
| 6,843,799 B2 | 1/2005 | Bartlett |
| 6,852,128 B2 | 2/2005 | Lange |
| 6,860,895 B1 | 3/2005 | Akerfeldt et al. |
| 6,878,155 B2 | 4/2005 | Sharkey et al. |
| 6,878,167 B2 | 4/2005 | Ferree |
| 6,883,520 B2 | 4/2005 | Lambrecht et al. |
| 6,893,462 B2 | 5/2005 | Buskirk et al. |
| 6,896,675 B2 | 5/2005 | Leung et al. |
| 6,911,034 B2 | 6/2005 | Nobles et al. |
| 6,913,622 B2 | 7/2005 | Gjunter |
| 6,923,823 B1 | 8/2005 | Bartlett et al. |
| 6,932,833 B1 | 8/2005 | Sandoval et al. |
| 6,936,070 B1 | 8/2005 | Muhanna |
| 6,936,072 B2 | 8/2005 | Lambrecht et al. |

(56) References Cited

U.S. PATENT DOCUMENTS

| | | |
|---|---|---|
| 6,960,215 B2 | 11/2005 | Olson, Jr. et al. |
| 6,964,674 B1 | 11/2005 | Matsuura et al. |
| 6,966,910 B2 | 11/2005 | Ritland |
| 6,966,931 B2 | 11/2005 | Huang |
| 6,969,404 B2 | 11/2005 | Ferree |
| 6,972,027 B2 | 12/2005 | Fallin et al. |
| 6,974,479 B2 | 12/2005 | Trieu |
| 6,980,862 B2 | 12/2005 | Fredricks et al. |
| 6,984,241 B2 | 1/2006 | Lubbers et al. |
| 6,984,247 B2 | 1/2006 | Cauthen |
| 6,997,956 B2 | 2/2006 | Cauthen |
| 7,001,431 B2 | 2/2006 | Bao et al. |
| 7,004,959 B2 | 2/2006 | Bonutti |
| 7,004,970 B2 | 2/2006 | Cauthen III et al. |
| 7,033,393 B2 | 4/2006 | Gainor et al. |
| 7,033,395 B2 | 4/2006 | Cauthen |
| 7,037,334 B1 | 5/2006 | Hlavka et al. |
| 7,052,516 B2 | 5/2006 | Cauthen, III et al. |
| 7,083,638 B2 | 8/2006 | Foerster |
| 7,094,258 B2 | 8/2006 | Lambrecht et al. |
| 7,147,651 B2 | 12/2006 | Morrison et al. |
| 7,189,235 B2 | 3/2007 | Cauthen |
| 7,217,279 B2 | 5/2007 | Reese |
| 7,223,289 B2 | 5/2007 | Trieu et al. |
| 7,280,865 B2 | 10/2007 | Adler |
| 7,285,124 B2 | 10/2007 | Foerster |
| 7,306,417 B2 | 12/2007 | Dorstewitz |
| 7,309,337 B2 | 12/2007 | Colleran et al. |
| 7,318,840 B2 | 1/2008 | McKay |
| 7,320,701 B2 | 1/2008 | Haut et al. |
| 7,322,978 B2 | 1/2008 | West, Jr. |
| 7,329,272 B2 | 2/2008 | Burkhart et al. |
| 7,331,982 B1 | 2/2008 | Kaiser et al. |
| 7,344,539 B2 | 3/2008 | Serhan et al. |
| 7,367,978 B2 | 5/2008 | Drewry et al. |
| 7,371,253 B2 | 5/2008 | Leung et al. |
| 7,390,332 B2 | 6/2008 | Selvitelli et al. |
| 7,399,018 B1 | 7/2008 | Khachaturian |
| 7,410,489 B2 | 8/2008 | Dakin et al. |
| 7,445,634 B2 | 11/2008 | Trieu |
| 7,465,308 B2 | 12/2008 | Sikora et al. |
| 7,494,496 B2 * | 2/2009 | Swain ................ A61B 17/0401 606/151 |
| 7,500,983 B1 | 3/2009 | Kaiser et al. |
| 7,513,911 B2 | 4/2009 | Lambrecht et al. |
| 7,524,333 B2 | 4/2009 | Lambrecht et al. |
| 7,556,640 B2 | 7/2009 | Foerster |
| 7,611,521 B2 | 11/2009 | Lubbers et al. |
| 7,651,509 B2 | 1/2010 | Bojarski et al. |
| 7,682,540 B2 | 3/2010 | Boyan et al. |
| 7,749,273 B2 | 7/2010 | Cauthen, III et al. |
| 7,758,611 B2 * | 7/2010 | Kato ................ A61B 17/0057 606/151 |
| 7,766,915 B2 | 8/2010 | Jackson |
| 7,766,923 B2 | 8/2010 | Catanese, III et al. |
| 7,766,939 B2 | 8/2010 | Yeung et al. |
| 7,846,162 B2 | 12/2010 | Nelson et al. |
| 7,875,058 B2 | 1/2011 | Holmes, Jr. |
| 7,905,903 B2 | 3/2011 | Stone et al. |
| 7,910,124 B2 | 3/2011 | Boyan et al. |
| 7,938,847 B2 | 5/2011 | Fanton et al. |
| 7,955,388 B2 | 6/2011 | Jensen et al. |
| 8,002,830 B2 | 8/2011 | Boyan et al. |
| 8,021,367 B2 | 9/2011 | Bourke et al. |
| 8,038,920 B2 | 10/2011 | Denoziere et al. |
| RE43,143 E | 1/2012 | Hayhurst |
| 8,100,141 B2 | 1/2012 | Slupecki et al. |
| 8,128,698 B2 | 3/2012 | Bentley et al. |
| 8,142,808 B2 | 3/2012 | Boyan et al. |
| 8,163,022 B2 | 4/2012 | Bentley et al. |
| 8,202,305 B2 | 6/2012 | Reiley |
| 8,318,192 B2 | 11/2012 | Boyan et al. |
| 8,486,436 B2 | 7/2013 | Boyan et al. |
| 8,652,172 B2 * | 2/2014 | Denham ............ A61B 17/0401 606/228 |
| 8,895,073 B2 | 11/2014 | Boyan et al. |
| 9,155,543 B2 | 10/2015 | Walsh et al. |
| 9,526,632 B2 | 12/2016 | Walsh et al. |
| 2001/0029399 A1 | 10/2001 | Ku |
| 2001/0041916 A1 * | 11/2001 | Bonutti ............ A61B 17/0401 606/232 |
| 2001/0051816 A1 * | 12/2001 | Enzerink ............ A61B 17/0401 606/232 |
| 2002/0032483 A1 | 3/2002 | Nicholson et al. |
| 2002/0077701 A1 | 6/2002 | Kuslich |
| 2002/0082698 A1 | 6/2002 | Parenteau et al. |
| 2002/0111688 A1 | 8/2002 | Cauthen |
| 2002/0123807 A1 | 9/2002 | Cauthen, III |
| 2002/0133179 A1 | 9/2002 | McDevitt et al. |
| 2002/0147461 A1 | 10/2002 | Aldrich et al. |
| 2002/0151979 A1 | 10/2002 | Lambrecht et al. |
| 2002/0173851 A1 | 11/2002 | McKay |
| 2002/0188297 A1 | 12/2002 | Dakin et al. |
| 2003/0008396 A1 | 1/2003 | Ku |
| 2003/0074075 A1 | 4/2003 | Thomas, Jr. et al. |
| 2003/0083662 A1 * | 5/2003 | Middleton ......... A61B 17/0401 606/323 |
| 2003/0105489 A1 * | 6/2003 | Eichhorn ........... A61B 17/0401 606/232 |
| 2003/0125807 A1 | 7/2003 | Lambrecht et al. |
| 2003/0130669 A1 * | 7/2003 | Damarati ........... A61B 17/0401 606/151 |
| 2003/0130694 A1 * | 7/2003 | Bojarski ............ A61B 17/0401 606/228 |
| 2003/0153976 A1 | 8/2003 | Cauthen, III et al. |
| 2003/0158604 A1 | 8/2003 | Cauthen, III et al. |
| 2003/0181983 A1 | 9/2003 | Cauthen |
| 2003/0195514 A1 | 10/2003 | Trieu et al. |
| 2003/0195628 A1 | 10/2003 | Bao et al. |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0039392 A1 | 2/2004 | Trieu |
| 2004/0054414 A1 | 3/2004 | Trieu et al. |
| 2004/0097980 A1 | 5/2004 | Ferree |
| 2004/0143329 A1 | 7/2004 | Ku |
| 2004/0153074 A1 | 8/2004 | Bojarski et al. |
| 2004/0162568 A1 * | 8/2004 | Saadat ................ A61B 1/00135 606/139 |
| 2004/0260397 A1 | 12/2004 | Lambrecht et al. |
| 2005/0033363 A1 | 2/2005 | Bojarski et al. |
| 2005/0033440 A1 | 2/2005 | Lambrecht et al. |
| 2005/0038519 A1 | 2/2005 | Lambrecht et al. |
| 2005/0049592 A1 | 3/2005 | Keith et al. |
| 2005/0049704 A1 | 3/2005 | Jackson |
| 2005/0049708 A1 | 3/2005 | Atkinson et al. |
| 2005/0060038 A1 | 3/2005 | Lambrecht et al. |
| 2005/0071003 A1 | 3/2005 | Ku |
| 2005/0106255 A1 | 5/2005 | Ku |
| 2005/0149197 A1 | 7/2005 | Cauthen |
| 2005/0159812 A1 * | 7/2005 | Dinger ................ A61F 2/0811 623/13.14 |
| 2005/0234512 A1 | 10/2005 | Nakao |
| 2005/0256582 A1 | 11/2005 | Ferree |
| 2005/0278025 A1 | 12/2005 | Ku et al. |
| 2005/0283246 A1 | 12/2005 | Cauthen et al. |
| 2006/0060038 A1 | 3/2006 | Sammartin |
| 2006/0084994 A1 | 4/2006 | Atkinson et al. |
| 2006/0100711 A1 | 5/2006 | Cauthen |
| 2006/0122608 A1 * | 6/2006 | Fallin ................ A61B 17/0401 606/232 |
| 2006/0129156 A1 | 6/2006 | Cauthen et al. |
| 2006/0129245 A1 | 6/2006 | Cauthen |
| 2006/0142864 A1 | 6/2006 | Cauthen |
| 2006/0161258 A1 | 7/2006 | Cauthen |
| 2006/0167553 A1 | 7/2006 | Cauthen et al. |
| 2006/0173545 A1 | 8/2006 | Cauthen et al. |
| 2006/0190042 A1 | 8/2006 | Stone et al. |
| 2006/0190085 A1 | 8/2006 | Cauthen |
| 2006/0241773 A1 | 10/2006 | Cauthen |
| 2006/0253152 A1 | 11/2006 | Evans et al. |
| 2006/0287731 A1 | 12/2006 | Cauthen et al. |

(56) References Cited

U.S. PATENT DOCUMENTS

| | | |
|---|---|---|
| 2007/0061012 A1 | 3/2007 | Cauthen |
| 2007/0061013 A1 | 3/2007 | Cauthen Iii et al. |
| 2007/0071568 A1 | 3/2007 | Dorstewitz |
| 2007/0073407 A1 | 3/2007 | Cauthen et al. |
| 2007/0083236 A1 | 4/2007 | Sikora et al. |
| 2007/0088438 A1 | 4/2007 | Cauthen Iii et al. |
| 2007/0100348 A1 | 5/2007 | Cauthen et al. |
| 2007/0100354 A1 | 5/2007 | Cauthen Iii et al. |
| 2007/0118226 A1 | 5/2007 | Lambrecht et al. |
| 2007/0156244 A1 | 7/2007 | Cauthen |
| 2007/0156245 A1 | 7/2007 | Cauthen et al. |
| 2007/0185497 A1 | 8/2007 | Cauthen et al. |
| 2007/0185532 A1* | 8/2007 | Stone ............... A61B 17/0401 606/232 |
| 2007/0198021 A1 | 8/2007 | Wales |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0288041 A1 | 12/2007 | Cauthen |
| 2007/0299540 A1 | 12/2007 | Ku |
| 2008/0033561 A1 | 2/2008 | Cauthen |
| 2008/0082128 A1 | 4/2008 | Stone |
| 2008/0086138 A1* | 4/2008 | Stone ............... A61B 17/0401 606/265 |
| 2008/0140092 A1* | 6/2008 | Stone ............... A61B 17/0401 606/144 |
| 2008/0147127 A1 | 6/2008 | Tipirneni et al. |
| 2008/0255613 A1 | 10/2008 | Kaiser et al. |
| 2009/0024165 A1 | 1/2009 | Ferree |
| 2009/0036893 A1 | 2/2009 | Kartalian et al. |
| 2009/0062854 A1 | 3/2009 | Kaiser et al. |
| 2009/0131936 A1 | 5/2009 | Tipirneni et al. |
| 2009/0131991 A1 | 5/2009 | Tipirneni et al. |
| 2009/0138042 A1* | 5/2009 | Thal ............... A61B 17/0401 606/232 |
| 2009/0259260 A1 | 10/2009 | Bentley et al. |
| 2009/0306711 A1* | 12/2009 | Stone ............... A61B 17/0401 606/232 |
| 2009/0318961 A1 | 12/2009 | Stone et al. |
| 2010/0016892 A1* | 1/2010 | Kaiser ............... A61B 17/0401 606/232 |
| 2010/0016894 A1 | 1/2010 | Houard et al. |
| 2010/0036389 A1* | 2/2010 | Schwartz ........... A61B 17/0401 606/108 |
| 2010/0198258 A1 | 8/2010 | Heaven et al. |
| 2010/0318125 A1 | 12/2010 | Gerber et al. |
| 2011/0004242 A1 | 1/2011 | Stchur |
| 2011/0118780 A1 | 5/2011 | Holmes, Jr. |
| 2011/0118796 A1 | 5/2011 | Reiley et al. |
| 2011/0172682 A1 | 7/2011 | Brady et al. |
| 2011/0172701 A1 | 7/2011 | Wales et al. |
| 2011/0224729 A1 | 9/2011 | Baker et al. |
| 2011/0257652 A1 | 10/2011 | Roman |
| 2012/0016426 A1 | 1/2012 | Robinson |
| 2012/0089193 A1* | 4/2012 | Stone ............... A61B 17/0401 606/301 |
| 2012/0101502 A1 | 4/2012 | Kartalian et al. |
| 2012/0165864 A1* | 6/2012 | Hernandez ......... A61B 17/0401 606/232 |
| 2012/0165938 A1* | 6/2012 | Denham ............ A61B 17/0401 623/13.14 |
| 2013/0006368 A1 | 1/2013 | Walsh et al. |
| 2013/0012765 A1 | 1/2013 | Vemuri et al. |
| 2013/0012942 A1 | 1/2013 | Nelson et al. |
| 2013/0096611 A1* | 4/2013 | Sullivan ............ A61B 17/0485 606/232 |
| 2013/0211451 A1 | 8/2013 | Wales et al. |
| 2013/0253581 A1* | 9/2013 | Robison ............ A61B 17/0401 606/232 |
| 2014/0081325 A1* | 3/2014 | Sengun ............. A61B 17/0401 606/232 |
| 2014/0214080 A1 | 7/2014 | Wales et al. |
| 2015/0351815 A1 | 12/2015 | Wales et al. |

FOREIGN PATENT DOCUMENTS

| | | |
|---|---|---|
| EP | 0025706 | 3/1981 |
| EP | 0049978 | 4/1982 |
| EP | 0076409 | 4/1983 |
| EP | 0110316 | 6/1984 |
| EP | 0122902 | 10/1984 |
| EP | 0126570 | 11/1984 |
| EP | 0145577 | 6/1985 |
| EP | 0042953 | 9/1985 |
| EP | 0193784 | 9/1986 |
| EP | 1108401 | 6/2001 |
| EP | 1743587 | 1/2007 |
| EP | 1797827 | 6/2007 |
| EP | 1857055 | 11/2007 |
| GB | 2054383 | 2/1981 |
| WO | WO 91/16867 | 11/1991 |
| WO | WO 94/23671 | 10/1994 |
| WO | WO 95/22285 | 8/1995 |
| WO | WO 95/31946 | 11/1995 |
| WO | WO 95/31948 | 11/1995 |
| WO | WO 96/27339 | 9/1996 |
| WO | WO 97/20874 | 6/1997 |
| WO | WO 97/26847 | 7/1997 |
| WO | WO 98/01091 | 1/1998 |
| WO | WO 98/05274 | 2/1998 |
| WO | WO 98/22050 | 5/1998 |
| WO | WO 98/20939 | 9/1998 |
| WO | WO 99/00074 | 1/1999 |
| WO | WO 99/02108 | 1/1999 |
| WO | WO 99/04720 | 2/1999 |
| WO | WO 99/16381 | 4/1999 |
| WO | WO 99/61084 | 12/1999 |
| WO | WO 00/20021 | 4/2000 |
| WO | WO 00/25706 | 5/2000 |
| WO | WO 00/42953 | 7/2000 |
| WO | WO 00/49978 | 8/2000 |
| WO | WO 00/61037 | 10/2000 |
| WO | WO 00/62832 | 10/2000 |
| WO | WO 00/76409 | 12/2000 |
| WO | WO 01/10316 | 2/2001 |
| WO | WO 01/12107 | 2/2001 |
| WO | WO 01/21246 | 3/2001 |
| WO | WO 01/22902 | 4/2001 |
| WO | WO 01/25670 | 4/2001 |
| WO | WO 01/28464 | 4/2001 |
| WO | WO 01/45577 | 6/2001 |
| WO | WO 01/93784 | 12/2001 |
| WO | WO 01/95818 | 12/2001 |
| WO | WO 02/17825 | 3/2002 |
| WO | WO 2007/135101 | 11/2007 |
| WO | WO 2009/100242 | 8/2009 |
| WO | WO 2010/088561 | 8/2010 |
| WO | PCT/US2013/025147 | 2/2013 |
| WO | WO 2013/119812 | 8/2013 |
| WO | PCT/US2014/013242 | 1/2014 |
| WO | WO 2014/117107 | 7/2014 |
| WO | PCT/US2016/027370 | 4/2015 |
| WO | PCT/US2016/025080 | 3/2016 |
| WO | PCT/US2016/025081 | 3/2016 |

OTHER PUBLICATIONS

U.S. Appl. No. 11/053,410, filed Feb. 7, 2005, Surface Directed Cellular Attachment.
U.S. Appl. No. 12/117,673, filed May 8, 2008, Method of Treating Joints with Hydrogel Implants.
U.S. Appl. No. 12/117,667, filed May 8, 2008, Method of Making Hydrogel Implants.
U.S. Appl. No. 13/427,648, filed Mar. 22, 2012, Articular Joint Implant.
U.S. Appl. No. 11/053,409, filed Feb. 7, 2005, Load Bearing Biocompatible Device.

(56) References Cited

OTHER PUBLICATIONS

U.S. Appl. No. 12/273,429, filed Nov. 18, 2008, Load Bearing Hydrogel Implants for Treating Joints.
U.S. Appl. No. 12/273,450, filed Nov. 18, 2008, Method of Making Load Bearing Hydrogel Implants.
U.S. Appl. No. 13/052,826, filed Mar. 21, 2011, Hydrogel Implant With Superficial Pores.
U.S. Appl. No. 08/932,029, filed Sep. 17, 1997, Poly(Vinyl Alcohol) Cryogel.
U.S. Appl. No. 09/271,032, filed Mar. 17, 1999, Poly(Vinyl Alcohol) Hydrogel.
U.S. Appl. No. 09/846,788, filed May 1, 2001, Poly(Vinyl Alcohol) Cryogel.
U.S. Appl. No. 10/199,554, filed Jul. 19, 2002, Poly(Vinyl Alcohol) Hydrogel.
U.S. Appl. No. 10/966,859, filed Oct. 14, 2004, Poly(Vinyl Alcohol) Hydrogel.
U.S. Appl. No. 10/966,866, filed Oct. 14, 2004, Poly(Vinyl Alcohol) Hydrogel.
U.S. Appl. No. 10/752,246, filed Jan. 5, 2004, Poly(Vinyl Alcohol) Hydrogel.
U.S. Appl. No. 11/837,027, filed Aug. 10, 2007, Method of Making Medical Implants of Poly(Vinyl Alcohol) Hydrogel.
U.S. Appl. No. 10/865,238, filed Jun. 10, 2004, Meniscus Prosthesis.
U.S. Appl. No. 13/553,508, filed Jul. 19, 2012, Meniscus Prosthesis.
U.S. Appl. No. 11/626,405, filed Jan. 24, 2007, Method of Producing PVA Hydrogel Implants and Related Devices.
U.S. Appl. No. 13/480,272, filed May 24, 2012, Tapered Joint Implant and Related Tools.
U.S. Appl. No. 14/826,918, filed Aug. 14, 2015, Methods of Repairing a Joint Using a Wedge-Shaped Implant.
U.S. Appl. No. 15/386,756, filed Dec. 21, 2016, Devices and Methods for Creating Wedge-Shaped Recesses.
U.S. Appl. No. 13/673,626, filed Nov. 9, 2012, Bone Anchor and Related Instrumentation and Methods.
U.S. Appl. No. 14/763,502, filed Jul. 24, 2015, Systems and Method for Orthopedic Repair.
U.S. Appl. No. 15/098,265, filed Apr. 13, 2016, Tooling for Creating Tapered Opening in Tissue and Related Methods.
U.S. Appl. No. 15/085,840, filed Mar. 30, 2016, Hydrogel Implants with Porous Materials and Methods.
U.S. Appl. No. 15/085,796, filed Mar. 30, 2016, Carpometacarpal (CMC) Implants and Methods.
Surgical Technique for "PRO-TOE™ VO Hammertoe Fixation System" by Wright Medical Technology, Inc. in 12 pages (dated 2011 and retrieved on or about May 2015).
Surgical Technique for "Hammertoe PIP Joint Arthrodesis using Trim-It Spin Pin™ Fixation" by Arthrex Inc. in 4 pages (dated 2014 and retrieved on or about May 2015).
Camasta, C.A., et al., "Buried Kirschner-Wire Fixation for Hammertoe Arthrodesis," in: S.J. Miller (Ed.) Reconstructive Surgery of the Foot and Leg. Update 2008. Podiatry Institute, Tucker (GA); 2008 (pp. 5-8).
U.S. Appl. No. 12/117,673, filed May 8, 2008 Method of Treating Joints with Hydrogel Implants.

\* cited by examiner

METHOD AND SYSTEM FOR ORTHOPEDIC REPAIR

CROSS-REFERENCE TO RELATED APPLICATIONS

This application claims priority benefit of U.S. Provisional Application No. 61/757,553, filed Jan. 28, 2013, the entirety of which is hereby incorporated by reference herein.

TECHNICAL FIELD

The present invention relates to medical devices and methods for the orthopedic repair to correct a deformity. More specifically, the invention relates to devices and methods for stabilizing, supporting, and compressing adjacent bones to eliminate motion and promote fusion.

BACKGROUND

Bone or joint fusion surgery, called arthrodesis, is performed to relieve arthritis pain in the ankles, wrists, fingers, thumbs, or spine. In arthrodesis, two bones on each end of a joint are fused, eliminating the joint itself. Joint fusion surgery can be used in patients whose joints have eroded or have been destroyed by osteoarthritis, rheumatoid arthritis, or other forms of arthritis. There are different ways to perform joint fusion surgery. In one procedure, bone graft can be taken from another part of the body or from a bone bank and placed in between the two bones being fused to stimulate the fusion. Recently, a variety of synthetic bone substitutes have been made available with osteoinductive properties to facilitate bone forming. In another procedure, implants of metal plates, screws, or wires can be used to hold the bones together in a position which favors bone growth. Over time, the body heals the bones to become one, but occasionally a bone graft may be needed to aid healing. While a fused joint loses flexibility, it can bear weight better, is more stable, and in many cases significantly less painful.

SUMMARY

In Example 1, an embodiment of the present invention is an implantable orthopedic repair device which includes an implant body having a rigid tubular shape which defines an inner lumen and an orthogonal suture side hole in communication with the inner lumen. The implantable orthopedic repair device includes a tension assembly that is supported by the inner lumen and suture side hole of the implant body. The tension assembly includes a suture loop which defines a suture tail which passes through the suture side hole and forms sliding knot within the inner lumen of the implant body. When the suture is tensioned, the suture loop contracts at least one bone anchor, independent of the implant body, unidirectionally towards the implant body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
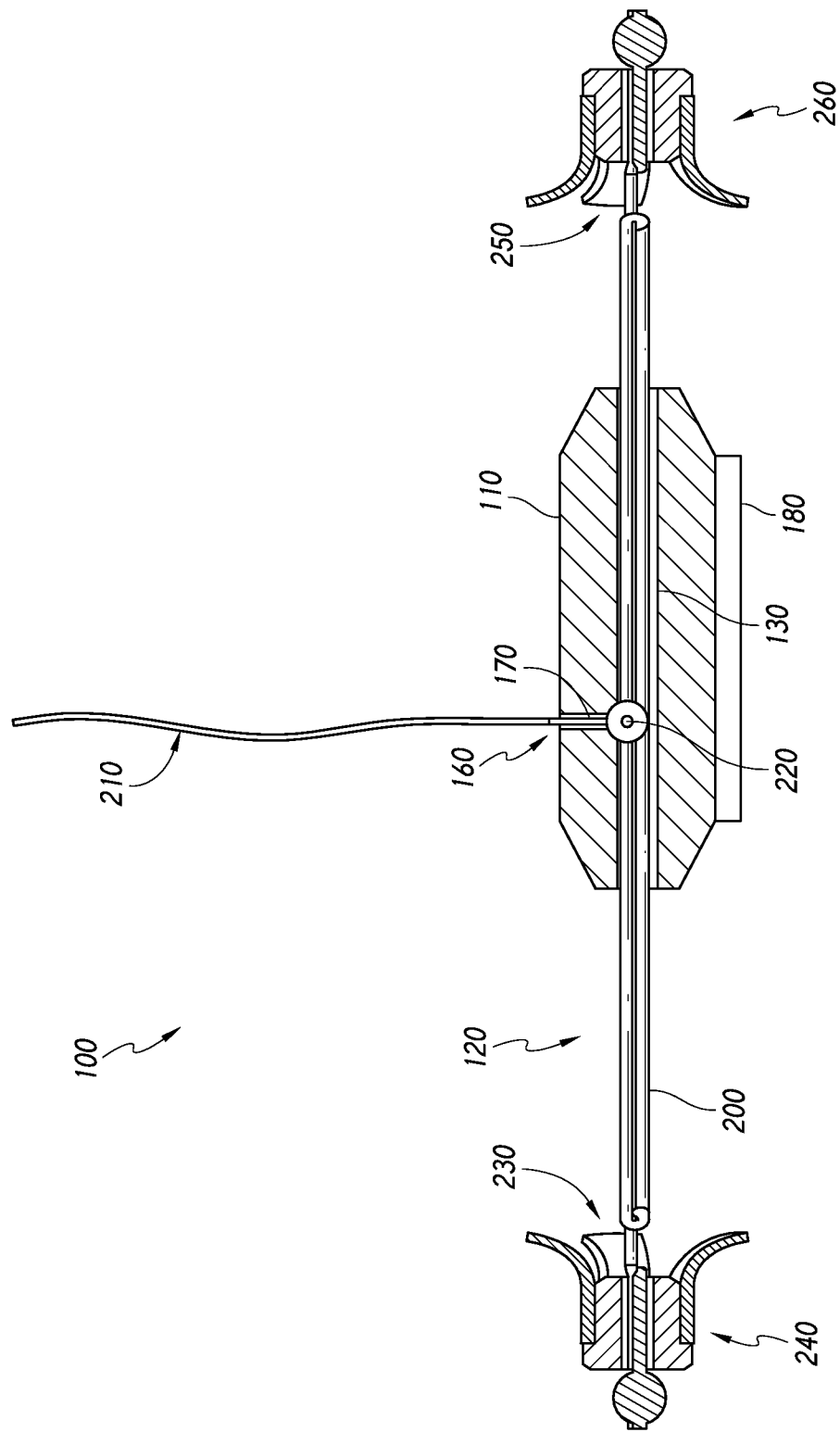
FIG. 1 is a cross-sectional illustration of an embodiment of an implantable orthopedic repair implant.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The implantable orthopedic repair implant comprises of two elements: an implant body and a tension assembly. The implant body is a rigid tubular support element that provides stability to help join two adjacent bones together. The body of the support element can be made from a rigid polymer, biocompatible, bioresorbable, osteoinductive material, or the link that is radiolucent. The implant body has an internal lumen through which the tension assembly runs. The implant body includes ribs the run the length of the body in a longitudinal direction which add rigidity and prevent rotational movement once embedded into bone. The tension assembly is made up of an adjustable suture loop that has pre-attached bone anchoring elements arranged on opposite sides of a sliding knot. The adjustable loop and sliding knot run through the internal lumen of the implant body. The combination of the implant body to support the tension assembly allows a physician to place the rigid implant body into each bone thus stabilizing the two bones adjacent to one another. The suture loop of the tension assembly draws the two bone anchors together thus creating compression between the two adjacent bones. The support, stability and compression help promote healing and bone growth.

The tensioning of suture loop requires the physician to pull on a suture tail of the suture assembly which, in turn, shortens the suture loop between the opposing bone anchors and thus drawing the anchors closer to the implant body. The fingers or barbs on the bone anchor are arranged such that they grab or fixate to the bone structure. The implant body has a suture hole that runs through a side wall orthogonally to the internal lumen. The suture side hole forms an internal wall which acts as an internal knot pusher for the sliding knot. The out dimension of the sliding knot is larger than the suture side hole to ensure the sliding knot remains fixed.

Figure 2:
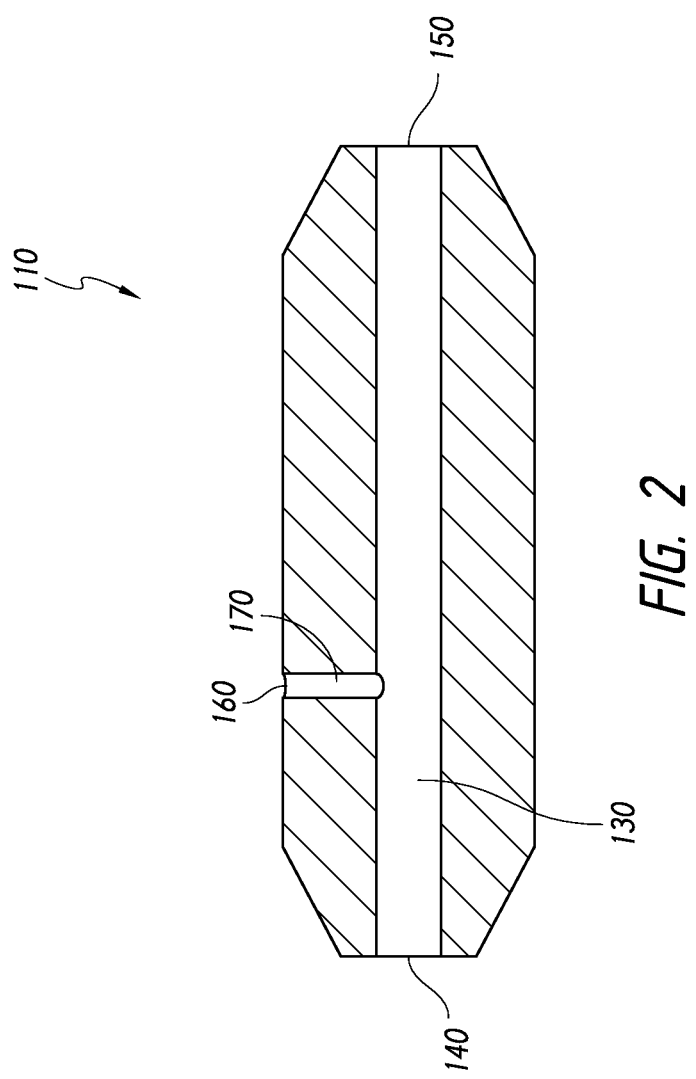
FIG. 2 is a cross-sectional illustration of an embodiment of an implant body of the implantable orthopedic repair implant in FIG. 1.

FIG. 1 is a cutaway illustration of an orthopedic implant 100 which includes an implant body 110 and a tension assembly 120. The implant body 110, as shown FIG. 2, includes a rigid tubular shape which defines an inner lumen 130 that runs longitudinally through the major axis of the implant body 110 to form a first and second open end 140, 150. Orthogonal to the inner lumen 130 is a suture side hole 160 which extends from the inner lumen 130 to the exterior of the implant body 110 forming an inner wall 170 which allows external access to the inner lumen 130 or, vice versa, internal access from the exterior of the implant body 110. The implant body 110 may include one or more ribs 180 the run the length of the implant body 110 in a longitudinal direction to add rigidity and prevent rotational movement once embedded into bone.

Figure 3:
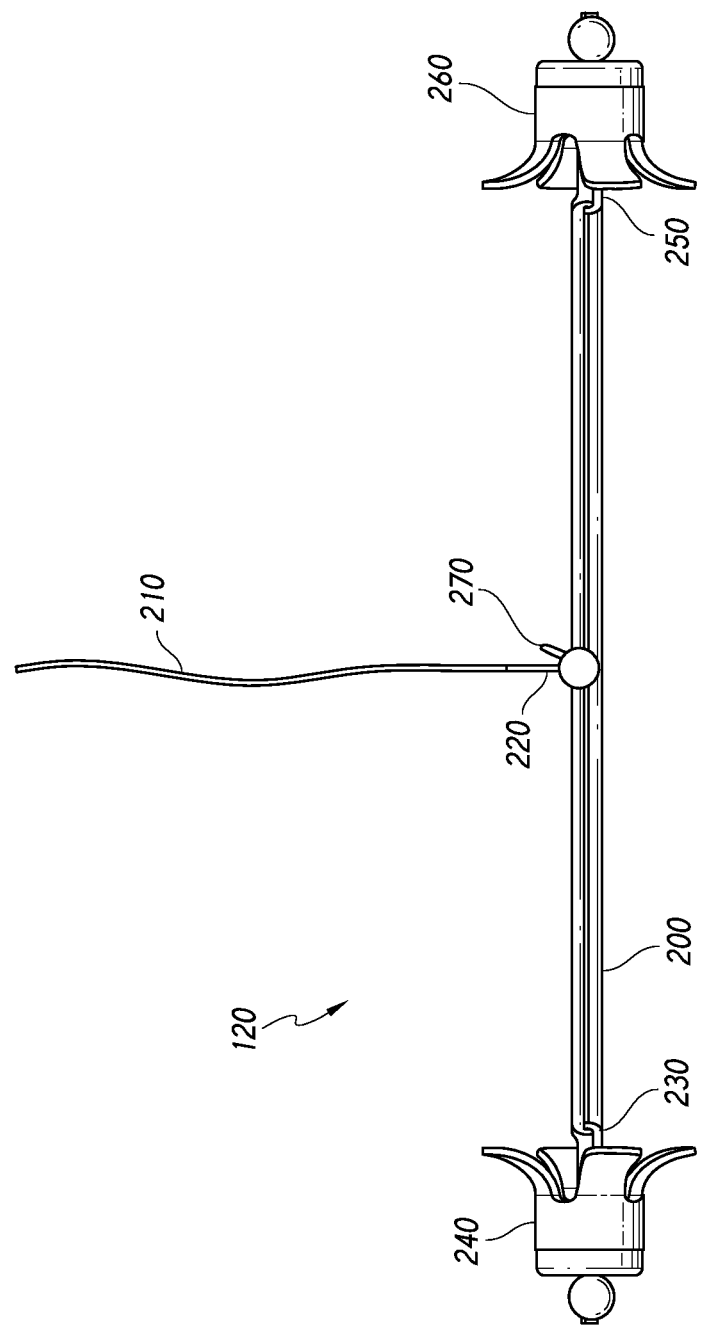
FIG. 3 is a perspective illustration of an embodiment of a tension assembly of the implantable orthopedic repair implant in FIG. 1.

FIG. 3 shows a perspective illustration of one embodiment of the tension assembly 120 which is supported by the implant body 110 as shown in FIG. 1. The tension assembly 120 includes a suture loop 200 that comprises a suture tail 210. The suture tail 210 passes through the suture side hole 160 and forms a sliding knot 220 which is held in place approximate to a junction where the inner lumen 130 and the suture side hole 160 meet. The outer dimensions of the sliding knot 220 are larger than the suture side hole 160 to ensure that the sliding knot 220 remains in a fixed position relative to the implant body 110. The suture side hole 160 is offset from a central axis of the implant body 110 to facilitate implantation.

The suture loop 200 continues from the formed sliding knot 220 through the inner lumen 130 beyond the first end 140 of the implant body 110. The suture loop 200 is then looped through a first eyelet 230 of a first bone anchor 240 back through the first end 140 and continues through the inner lumen 130 of the implant body 110 and beyond the second end 150 to a second eyelet 250 of a second bone anchor 260. The suture loop 200 is looped through the second eyelet 250 and fixedly terminated at a suture terminus 270 at or near the sliding knot 220. In this arrangement, as the suture tail 210 is tensioned or pulled away from the implant body 110, the suture loop 200 contracts the first and second bone anchors 240, 260 towards the respective first end 140 and second end 150 of the implant body 110. The sliding knot 220 is formed such that when opposing forces are applied on the sliding knot 220 longitudinally the knot tightens to ensure that the first and second anchors 240, 260 travel unidirectionally towards the implant body 110 and remains fixed due to the opposing force generated by the bone anchors.

The suture loop 200 is adjustable when the sliding knot 220 is held in a fixed position, for example within the inner lumen 130 adjacent to the suture side hole 140. As the suture tail 210 is tensioned or pulled away from the implant body 110, the tension between the bone anchors 240, 260 is increased and thus the distance between the bone anchors can be shortened. It should be noted that size and shape of the orthopedic implant 100 can be adapted according to a plurality of applications. For example, the implant 100 can be adapted for fusing bones in the hand and foot and such will be smaller than an adaptation for fusing adjacent cervical bones in the spine or neck. The size and shape of the implant body 110, bone anchors 240, 260, suture loop length or thickness, and the like can be adapted according to a corresponding implant location and application.

Figure 4:
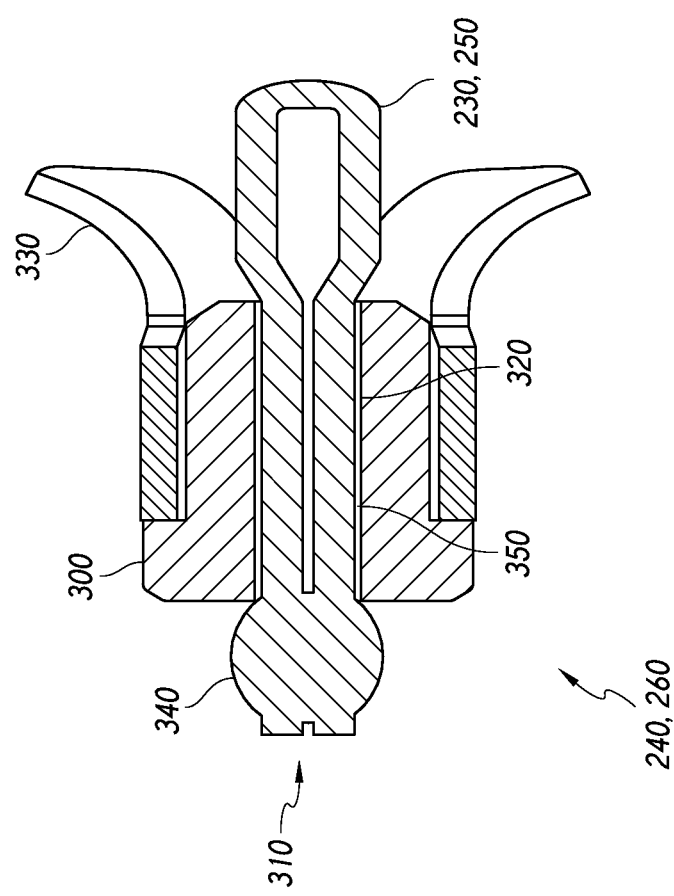
FIG. 4 is a cross-sectional illustration of an embodiment of a bone anchor of the implantable orthopedic repair implant in FIG. 1.

With reference to FIG. 4, each of the bone anchors 240, 260 includes an outer anchor tube 300 and an insert 310. The anchor tube 300 defines a longitudinal channel 320 which accepts the insert 310. The anchor tube includes a plurality of barbs or fingers 330 arranged radially about the anchor tube 300. Each barb 330 extends from the anchor tube 300 outwards and is configured to engage bone at the implantation site for securing the bone anchor therein to form an expandable interference fit. The insert 310 includes a head 340 and a shank 350 extending longitudinally from the head through the anchor tube 300. At the end of the shank 350 opposite the head 340 is the eyelet 230, 250. The eyelet 230, 250 permits the suture loop 200 to traverse through eyelet 230, 250 as the suture tail 210 is tensioned. It should be noted that other types of bone anchors can be used to with the orthopedic implant 100 which have eyelets configured to permit the suture loop 200 travel freely through, e.g., screw-in bone anchors with various thread arrangements in addition to other interference fit bone anchors with various arrangements and the like.

During an arthrodesis procedure, portions of a pair of adjacent bones to selected to be fused that create the joint are resected and a bore hole is drilled into each the adjacent bones such that are substantially parallel and opposing. The drilled holes are large enough to accept a cannula which delivers one or more bone anchors. During insertion, the bone anchor 240, 260 is disposed within the cannula such that the barbs are deflected radially inwards towards the longitudinal axis of the bone anchor 240, 260. The cannula is withdrawn proximally to release the bone anchor 240, 260 therefrom. Once released from the cannula, the barbs of the bone anchor 240, 260 anchor tube self-expand radially outward to bear against and engage the bone forming the wall of the bore hole to secure the bone anchor 240, 260 therein. The bore hole is drilled deep enough into the bone to accept the entire bone anchor 240, 260 and a portion of the implant body 110.

As previously described, the suture side hole 140 is offset from the central axis of the implant body 110. In this manner, the bore hole that accepts the second bone anchor 260 will be longer to accept a greater portion of the implant body 110. Therefore, the bore hole which accepts the first bone anchor 140 will be short and thus accept a shorter portion of the implant body 110. Ideally, the suture side hole 140 is positioned in the implant body 110 such that it coincides with an interface that is formed between the adjacent bones once they are pulled together. The offset arrangement of the suture side hole 140 facilitates implantation and reduces procedure time.

The first and second bone anchors 240, 260 and the implant body 110 can be arranged in the cannula in a pre-arranged manner such that second anchor 260 can be introduced into the corresponding bore hole and then the first bone anchor 240 can be introduced into the opposing bore hole. Then the cannula is proximally withdrawn and the suture tail 210 is exposed. The physician can then pull the suture tail 210 to draw the adjacent bones together.

Figure 5:
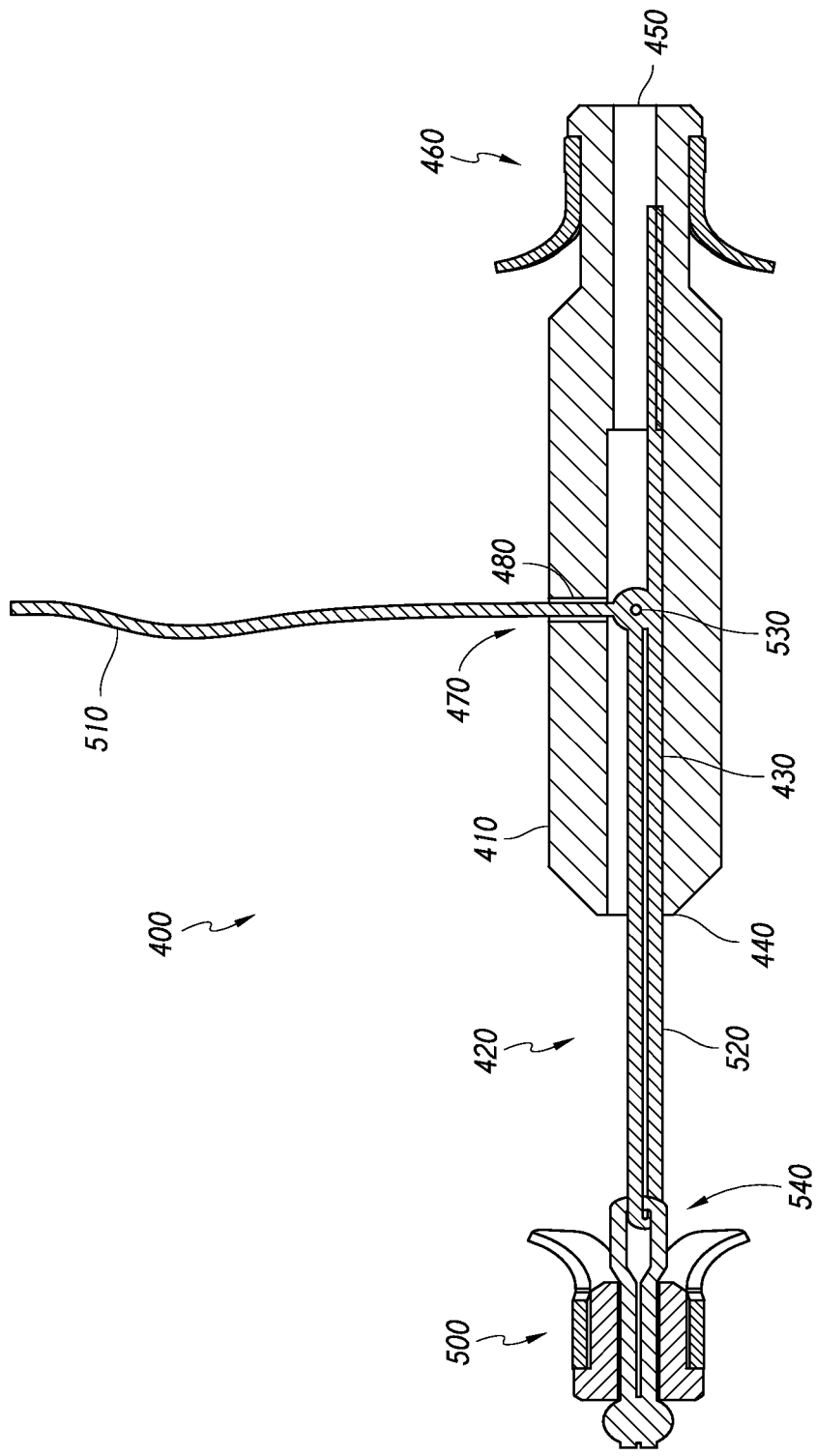
FIG. 5 is a cross-sectional illustration of another embodiment of an implantable orthopedic repair implant.

With reference to FIG. 5, another embodiment of orthopedic implant 400 is illustrated. Similarly to the embodiment of FIG. 1, the implant 400 includes an implant body 410 and a tension assembly 420. The implant body 410 includes a rigid tubular shape which defines an inner lumen 430 that runs longitudinally through the major axis of the implant body 410 to form a first open end 440 and second open end 450. The implant body 410 at the second open end 450 includes a bone anchor 460 integrated into the implant body 410. Orthogonal to the inner lumen 430 is a suture side hole 470 which extends from the inner lumen 430 to the exterior of the implant body 410 forming an inner wall 480 which allows external access to the inner lumen 430 or, vice versa, internal access from the exterior of the implant body 410.

Figure 6:
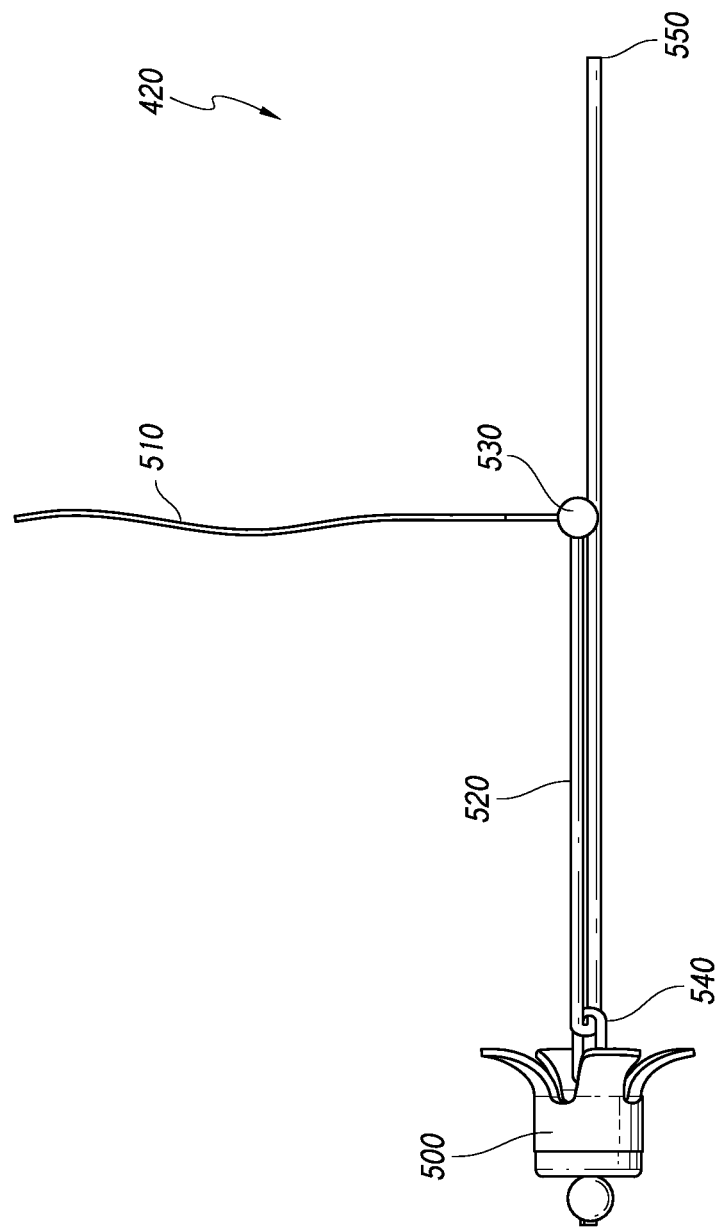
FIG. 6 is a perspective illustration of an embodiment of a tension assembly of the implantable orthopedic repair implant in FIG. 5.

The tension assembly 420 is illustrated in FIG. 6. In this embodiment, the tension assembly 420 includes one bone anchor 500 while the bone anchor 460 to be disposed in the opposing bore hole is integrated into the implant body 410. Similarly to the embodiment of FIG. 3, a suture tail 510 of a suture loop 520 passes through the suture side hole 470 and forms a sliding knot 530 which is fixedly held in place within the inner lumen 430 adjacent to suture side hole 470. The suture loop 520 continues from the formed sliding knot 530 through the inner lumen 430. The embodiments differ in that the suture loop 520 extends beyond the first open end 440 and is looped through an eyelet 540 of the bone anchor 500 and back through the first open end 440 and continues through the inner lumen 430 of the implant body 410 and is terminated at a suture terminus 550 which fixedly attached to the implant body 410. Since the opposing bone anchor 460 is integrated into the implant body 410, the suture loop 420 does pass through a second eyelet and then terminated. Rather, the suture loop passes through one eyelet 540 and is fixedly terminated within the implant body 410 at the suture terminus 550. The sliding knot 530 is formed such that when opposing forces are applied on the sliding knot 530 longitudinally the knot tightens to ensure that the bone anchor 500 and the implant body 410 remain fixed relative to one another.

Figure 7:
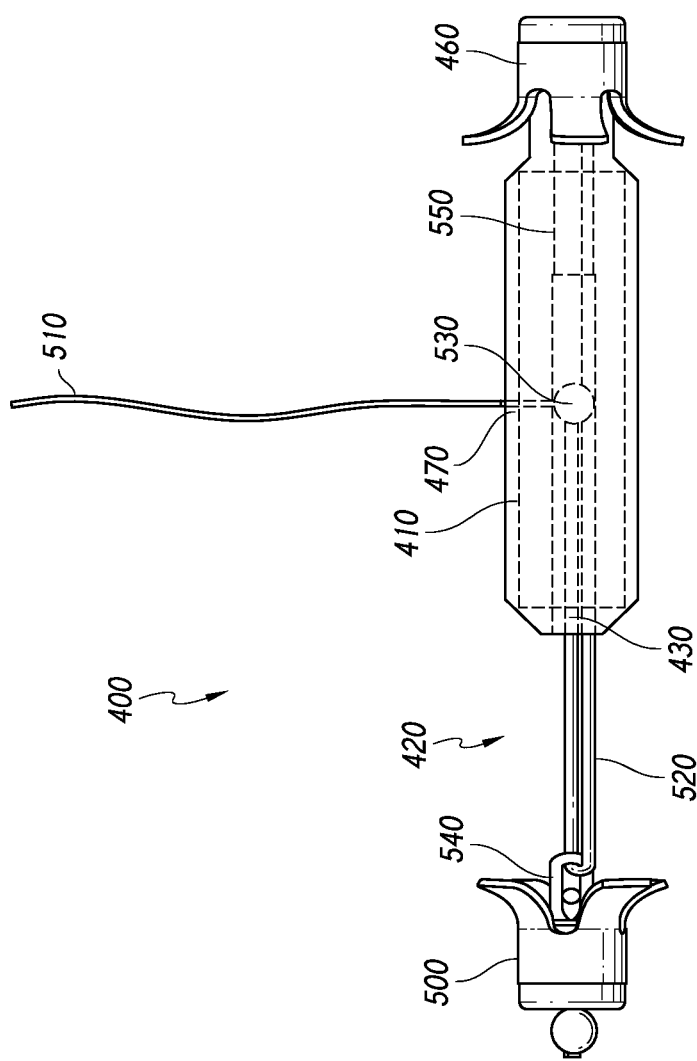
FIG. 7 is a perspective illustration of the implantable orthopedic repair implant of FIG. 5.

Unlike the embodiment of FIG. 1 which includes two bone anchors 240, 260 which are physically independent of the implant body 110, the implant 400 embodiment illustrated in FIG. 5 includes a single independent bone anchor 500 and a bone anchor 460 which is integrated into the implant body 410. This arrangement reduces the complexity of the implant 400 and improves rigidity and robustness of a planned orthopedic fusion. FIG. 7 is a perspective illustration of the orthopedic implant 400 including the implant body 410 and tension assembly 420.

Figure 8:
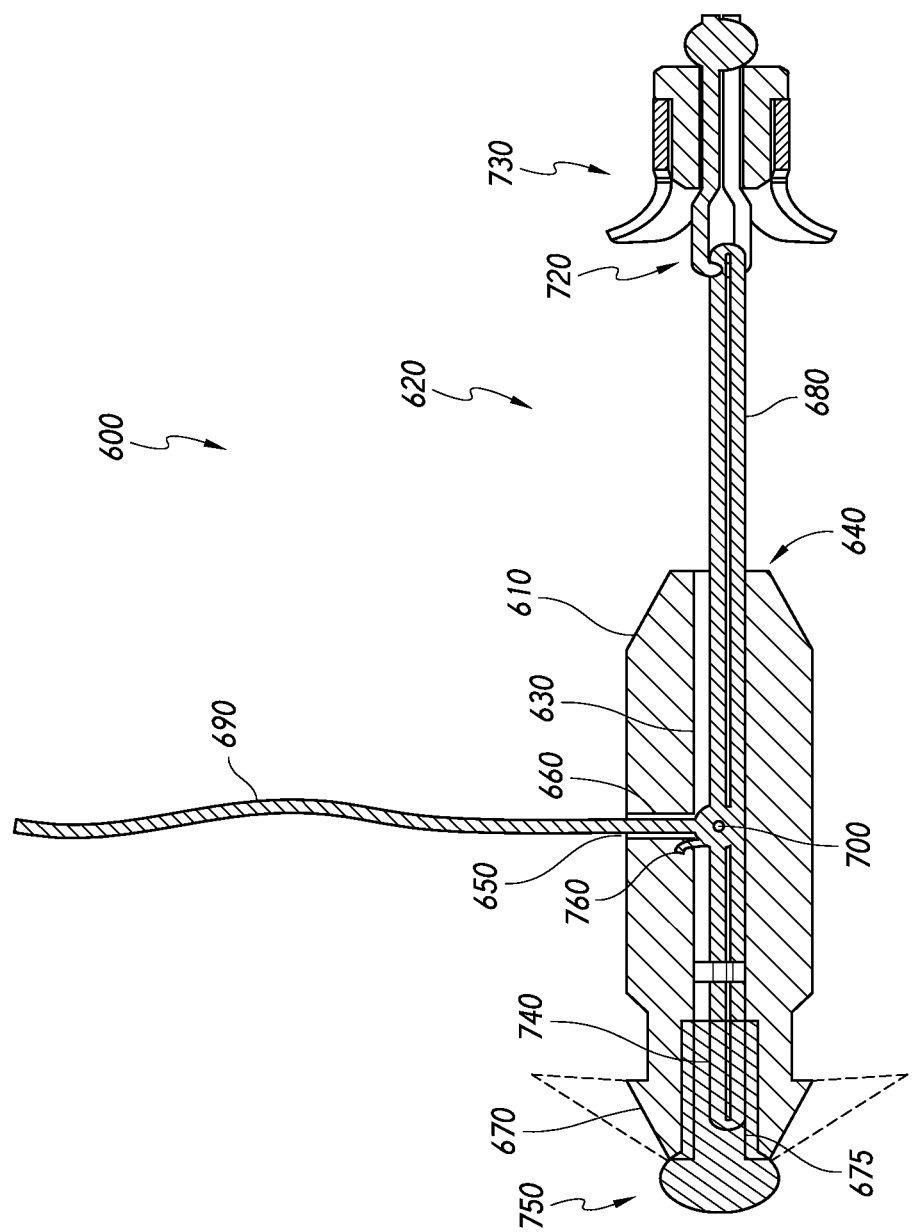
FIG. 8 is a cross-sectional illustration of another embodiment of an implantable orthopedic repair implant.

With reference to FIG. 8, another embodiment of orthopedic implant 600 is illustrated. The implant 600 includes an implant body 610 and a tension assembly 620. The implant body 610 includes a rigid tubular shape which defines an inner lumen 630 that runs longitudinally through the major axis of the implant body 410 to form an open end 640. Orthogonal to the inner lumen 630 is a suture side hole 650 which extends from the inner lumen 630 to the exterior of the implant body 610 forming an inner wall 660 which allows external access to the inner lumen 630 or, vice versa, internal access from the exterior of the implant body 610. Disposed at the end of the implant body 610 opposite the opening 640 is an expandable element 670 which when expanded is used to anchor the fixate the implant body 610 within a bore hole of a bone selected to be fused. The expanding element defines a longitudinal channel 675 which accepts an expanding insert that is slightly larger in diameter than the longitudinal channel 675. When the expanding insert is pulled into the longitudinal channel, the expanding element 670 is force radially outward, as shown by the dotted lines, into the sidewall of the bore hole in the bone creating an interference fit between the implant body 610 and the bone itself.

The tension assembly 620 includes a suture loop 680 with a suture tail 690 that passes through the suture side hole 650 and forms a sliding knot 700 which is fixedly held in place within the inner lumen 430 adjacent to suture side hole 470. The suture loop 680 continues from the formed sliding knot 700 through the inner lumen 630. The suture loop 680 extends beyond an open end 640 and is looped through an eyelet 720 of a bone anchor 730 and back through the open end 640 and continues through the inner lumen 630 of the implant body 410 through an eyelet 740 of a wedge 750 and is fixedly terminated at a suture terminus 550 at or near the sliding knot 220. The wedge 750 acts as an expanding insert to force the expanding element 670 radially outwards to engage the adjacent bone of the bore hole. The sliding knot 700 is formed such that when opposing forces are applied on the sliding knot 700 longitudinally the knot tightens to ensure that the bone anchor 730 and the wedge 750 remain fixed relative to one another.

In this arrangement, as the suture tail 690 is tensioned or pulled away from the implant body 610, the suture loop 680 contracts the bone anchor 730 towards the open end 640 and pulls the wedge 750 into the longitudinal channel 675 and the expanding element 760 is spread radially outward as shown by the dotted lines.

Figure 9:
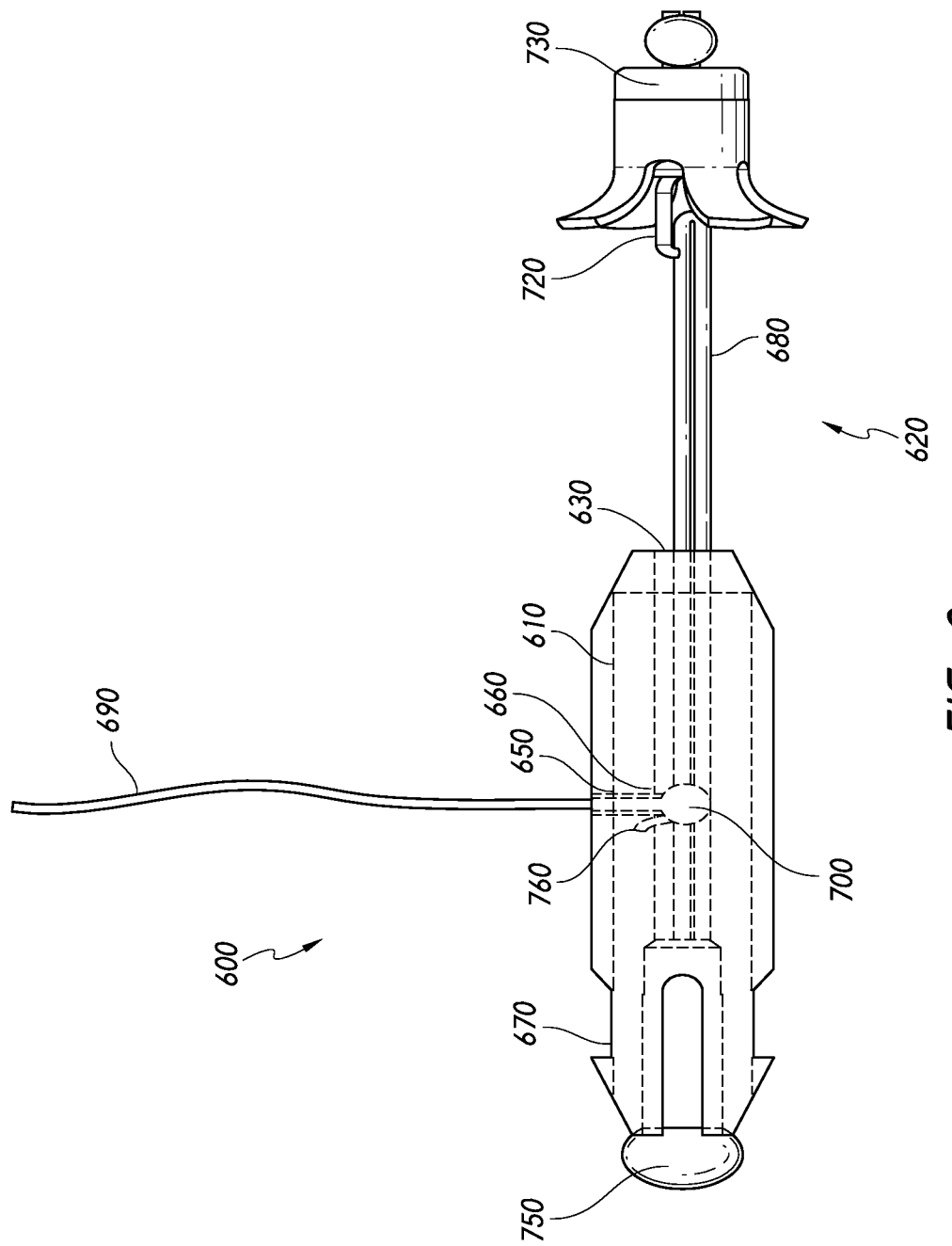
FIG. 9 is a perspective illustration of the implantable orthopedic repair implant of FIG. 8.

Since the expanding element 670 is integrated into the implant body 610, the entire implant body 610 forms an interference fit with the bore hole within the selected bone. This arrangement reduces the complexity of the implant 600 and improves rigidity and robustness of a planned orthopedic fusion. FIG. 9 is a perspective illustration of the orthopedic implant 600 including the implant body 610 and tension assembly 620.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable orthopedic repair device comprising:
   an implant body having a rigid tubular shape which defines an inner lumen and an orthogonal suture side hole, wherein the inner lumen runs longitudinally through a major axis of the implant body to form a first open end and second open end of the implant body;
   a first bone anchor adjacent the first open end of the implant body;
   a second bone anchor adjacent the second open end of the implant body; and
   a tension assembly supported by the inner lumen and suture side hole of the implant body, the tension assembly having a suture loop, the suture loop being coupled to the first bone anchor and the second bone anchor, wherein the suture loop defines a sliding knot and a suture tail that when tensioned through the suture side hole contracts the first bone anchor and the second bone anchor toward the implant body.

2. The device of claim 1, wherein the suture loop is connected to at least one of the first bone anchor and the second bone anchor using an eyelet.

3. The device of claim 1, wherein at least one of the first bone anchor and the second bone anchor comprises a plurality of barbs or fingers to help maintain tension between the first and second bone anchors when the suture tail of the tension assembly is tensioned.

4. The device of claim 1, wherein each of the first bone anchor and the second bone anchor comprises a plurality of barbs or fingers to help maintain tension between the first and second bone anchors when the suture tail of the tension assembly is tensioned.

5. The device of claim 1, wherein the suture side hole is offset from a central axis of the implant body to facilitate implantation.

6. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;
a first bone anchor adjacent the first open end of the implant body;
a second bone anchor adjacent the second open end of the implant body; and
a tension assembly positioned at least partially through the inner lumen;
wherein the tension assembly comprises a suture loop that extends from the first open end to the second open end of the implant body, the suture loop being coupled to the first bone anchor and the second bone anchor;
wherein a suture tail of the suture loop extends through a suture side hole of the implant body;
wherein the suture loop is configured to be tensioned via the suture tail; and
wherein when the suture tail is tensioned, the first bone anchor and the second bone anchor are drawn toward the implant body.

7. The device of claim 6, wherein the suture loop is connected to at least one of the first bone anchor and the second bone anchor using an eyelet.

8. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;
a first bone anchor adjacent the first open end of the implant body;
a second bone anchor adjacent the second open end of the implant body; and
a tension assembly positioned at least partially through the inner lumen;
wherein the tension assembly comprises a suture loop that extends from the first open end to the second open end of the implant body, the suture loop being coupled to the first bone anchor and the second bone anchor;
wherein a suture tail of the suture loop extends through a suture side hole of the implant body;
wherein the suture loop is configured to be tensioned via the suture tail;
wherein the suture loop comprises a sliding knot; and
wherein when the suture tail is tensioned, the first bone anchor and the second bone anchor are drawn toward the implant body.

9. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;
a first bone anchor adjacent the first open end of the implant body;
a second bone anchor adjacent the second open end of the implant body; and
a tension assembly positioned at least partially through the inner lumen;
wherein the tension assembly comprises a suture loop that extends from the first open end to the second open end of the implant body, the suture loop being coupled to the first bone anchor and the second bone anchor;
wherein a suture tail of the suture loop extends through a suture side hole of the implant body;
wherein the suture loop is configured to be tensioned via the suture tail;
wherein the suture loop comprises a sliding knot;
wherein when the suture tail is tensioned, the first bone anchor and the second bone anchor are drawn toward the implant body; and
wherein at least one of the first bone anchor and the second bone anchor comprises a plurality of barbs or fingers to help maintain tension between the first and second bone anchors when the suture tail of the tension assembly is tensioned.

10. The device of claim 9, wherein each of the first bone anchor and the second bone anchor comprises a plurality of barbs or fingers to help maintain tension between the first and second bone anchors when the suture tail of the tension assembly is tensioned.

11. The device of claim 6, wherein the suture side hole is offset from a central axis of the implant body to facilitate implantation.

12. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;
a bone anchor adjacent the first open end of the implant body; and
a tension assembly positioned at least partially through the inner lumen;
wherein the tension assembly comprises a suture loop that extends from the first open end to the second open end of the implant body, the suture loop being coupled to the bone anchor;
wherein a suture tail of the suture loop extends through a suture side hole of the implant body;
wherein the suture loop is configured to be tensioned via the suture tail; and
wherein when the suture tail is tensioned, the bone anchor is drawn toward the implant body.

13. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;
a bone anchor adjacent the first open end of the implant body; and
a tension assembly positioned at least partially through the inner lumen;
wherein the tension assembly comprises a suture loop that extends from the first open end to the second open end of the implant body, the suture loop being coupled to the bone anchor using an eyelet;
wherein a suture tail of the suture loop extends through a suture side hole of the implant body;
wherein the suture loop is configured to be tensioned via the suture tail; and
wherein when the suture tail is tensioned, the bone anchor is drawn toward the implant body.

14. An implantable orthopedic repair device comprising:
an implant body having a tubular shape that defines an inner lumen, wherein the inner lumen runs longitudinally through a major axis of the implant body to form a first open end and second open end of the implant body, wherein the implant body is rigid;

a bone anchor adjacent the first open end of the implant body; and a tension assembly positioned at least partially through the inner lumen;

wherein the tension assembly comprises a suture loop that extends from the first open end to the second open end of the implant body, the suture loop being coupled to the bone anchor using an eyelet;

wherein a suture tail of the suture loop extends through a suture side hole of the implant body;

wherein the suture loop is configured to be tensioned via the suture tail;

wherein when the suture tail is tensioned, the bone anchor is drawn toward the implant body; and wherein the suture loop comprises a sliding knot.

15. An implantable orthopedic repair device comprising:

an implant body having a tubular shape that defines an inner lumen, wherein the inner lumen runs longitudinally through a major axis of the implant body to form a first open end and second open end of the implant body, wherein the implant body is rigid;

a bone anchor adjacent the first open end of the implant body; and a tension assembly positioned at least partially through the inner lumen;

wherein the tension assembly comprises a suture loop that extends from the first open end to the second open end of the implant body, the suture loop being coupled to the bone anchor using an eyelet;

wherein a suture tail of the suture loop extends through a suture side hole of the implant body;

wherein the suture loop is configured to be tensioned via the suture tail;

wherein when the suture tail is tensioned, the bone anchor is drawn toward the implant body;

wherein the suture loop comprises a sliding knot; and wherein the bone anchor comprises a plurality of barbs or fingers to help maintain tension between the first and second bone anchors when the suture tail of the tension assembly is tensioned.

16. The device of claim 12, wherein the suture side hole is offset from a central axis of the implant body to facilitate implantation.

17. The device of claim 6, wherein each of the first bone anchor and the second bone anchor comprises a plurality of barbs or fingers to help maintain tension between the first and second bone anchors when the suture tail of the tension assembly is tensioned.

18. The device of claim 12, wherein the bone anchor comprises a plurality of barbs or fingers to help maintain tension along the device when the suture tail of the tension assembly is tensioned.

* * * * *